(12) United States Patent
King et al.

(10) Patent No.: US 11,753,472 B2
(45) Date of Patent: Sep. 12, 2023

(54) ANTIBODIES DIRECTED AGAINST T CELL IMMUNOGLOBULIN AND MUCIN PROTEIN 3 (TIM-3)

(71) Applicants: AnaptysBio, Inc., San Diego, CA (US); Tesaro, Inc., Waltham, MA (US)

(72) Inventors: David J. King, Encinitas, CA (US); Marilyn Kehry, San Diego, CA (US); Srimoyee Ghosh, Waltham, MA (US); Baochuan Huang, Waltham, MA (US)

(73) Assignees: Tesaro, Inc., Wilmington, DE (US); Anaptysbio, Inc., San Diego, CA (US)

( * ) Notice: Subject to any disclaimer, the term of this patent is extended or adjusted under 35 U.S.C. 154(b) by 0 days.

(21) Appl. No.: 17/512,257

(22) Filed: Oct. 27, 2021

(65) Prior Publication Data

US 2022/0169734 A1    Jun. 2, 2022

Related U.S. Application Data

(63) Continuation of application No. 16/346,463, filed as application No. PCT/US2017/059619 on Nov. 1, 2017, now abandoned.

(60) Provisional application No. 62/427,775, filed on Nov. 29, 2016, provisional application No. 62/416,131, filed on Nov. 1, 2016.

(51) Int. Cl.
| | | |
|---|---|---|
| *C07K 16/28* | (2006.01) | |
| *A61P 37/06* | (2006.01) | |
| *A61P 35/02* | (2006.01) | |
| *A61K 45/06* | (2006.01) | |

(52) U.S. Cl.
CPC .......... *C07K 16/2818* (2013.01); *A61P 35/02* (2018.01); *A61P 37/06* (2018.01); *C07K 16/2803* (2013.01); *C07K 16/2827* (2013.01); *A61K 45/06* (2013.01); *C07K 2317/41* (2013.01); *C07K 2317/524* (2013.01); *C07K 2317/53* (2013.01); *C07K 2317/70* (2013.01); *C07K 2317/76* (2013.01); *C07K 2317/92* (2013.01); *Y02A 50/30* (2018.01)

(58) Field of Classification Search
CPC ............ C07K 16/2818; C07K 16/2803; C07K 16/2827; A61P 37/06; A61P 35/02
See application file for complete search history.

(56) References Cited

U.S. PATENT DOCUMENTS

| | | |
|---|---|---|
| 4,828,981 A | 5/1989 | Maddio |
| 5,122,464 A | 6/1992 | Wilson et al. |
| 5,464,758 A | 11/1995 | Gossen et al. |
| 5,770,359 A | 6/1998 | Wilson et al. |
| 5,814,618 A | 9/1998 | Bujard et al. |
| 6,843,987 B2 | 1/2005 | Debets et al. |
| 7,112,715 B2 | 9/2006 | Chambon et al. |
| 8,008,449 B2 | 8/2011 | Korman et al. |
| 8,034,771 B2 | 10/2011 | Sims et al. |
| 8,101,176 B2 | 1/2012 | Kuchroo et al. |
| 8,168,757 B2 | 5/2012 | Finnefrock et al. |
| 8,481,021 B2 | 7/2013 | Sims et al. |
| 8,552,156 B2 | 10/2013 | Takayanagi et al. |
| 8,568,992 B2 | 10/2013 | Walker et al. |
| 8,841,418 B2 | 9/2014 | Karsunky et al. |
| 8,871,192 B2 | 10/2014 | Sims et al. |
| 9,023,995 B2 | 5/2015 | Brown et al. |
| 10,472,419 B2 | 11/2019 | Sabatos-Peyton et al. |
| 10,508,149 B2 | 12/2019 | Kehry et al. |
| 10,981,990 B2 | 4/2021 | Sabatos-Peyton et al. |
| 11,352,427 B2 | 6/2022 | Kehry et al. |
| 2003/0103985 A1 | 6/2003 | Adolf et al. |
| 2006/0134105 A1 | 6/2006 | Lazar et al. |
| 2008/0193465 A1 | 8/2008 | Dimitrov et al. |
| 2009/0093002 A1 | 4/2009 | Pfeifer et al. |
| 2009/0093024 A1 | 4/2009 | Bowers et al. |
| 2011/0159011 A1 | 6/2011 | Carrier et al. |
| 2011/0287485 A1 | 11/2011 | Bowers et al. |
| 2012/0189617 A1 | 7/2012 | Takayanagi et al. |
| 2012/0258495 A1 | 10/2012 | Gallo et al. |
| 2013/0022623 A1 | 1/2013 | Karsunky et al. |
| 2013/0156774 A1 | 6/2013 | Kuchroo et al. |
| 2013/0236471 A1 | 9/2013 | Brown et al. |
| 2013/0336982 A1 | 12/2013 | Mader et al. |
| 2014/0234330 A1 | 8/2014 | Budelsky et al. |
| 2014/0271627 A1 | 9/2014 | Puro |
| 2014/0294834 A1 | 10/2014 | Harms et al. |
| 2015/0017123 A1 | 1/2015 | Sims et al. |

(Continued)

FOREIGN PATENT DOCUMENTS

| | | |
|---|---|---|
| CN | 101516911 | 8/2009 |
| CN | 105209497 | 12/2015 |

(Continued)

OTHER PUBLICATIONS

Schiller, "Current Standards of Care in Small-Cell and Non-Small-Cell Lung Cancer", Oncology, Sep. 2001, 61:3-13.
Jemperli, Highlights of Prescribing Information, United States Prescribing Information, Apr. 2021, 23 pages.
Jemperli, Statement on a Nonproprietary Name Adopted by the USAN Council, United States Adopted Name, Nov. 29, 2017, 2 pages.

(Continued)

*Primary Examiner* — Amy E Juedes
*Assistant Examiner* — Peter Johansen
(74) *Attorney, Agent, or Firm* — Fish & Richardson P.C.

(57) ABSTRACT

Provided herein are anti-T Cell Immunoglobulin and Mucin Protein-3 (TIM 3) antibodies having particular immunoglobulin heavy chain polypeptide and immunoglobulin light chain polypeptide sequences and methods of using the anti-TIM-3 antibodies to treat a disorder or disease that is responsive to TIM-3 inhibition, such as cancer, an infectious disease, or an autoimmune disease.

19 Claims, 2 Drawing Sheets

Specification includes a Sequence Listing.

(56) References Cited

U.S. PATENT DOCUMENTS

| | | |
|---|---|---|
| 2015/0203584 A1 | 7/2015 | Brown et al. |
| 2015/0218274 A1* | 8/2015 | Sabatos-Peyton ........ A61P 1/16 435/254.2 |
| 2016/0137708 A1 | 5/2016 | Sims et al. |
| 2017/0121409 A1 | 5/2017 | Verona et al. |
| 2017/0190777 A1 | 7/2017 | Sabatos-Peyton et al. |
| 2018/0127500 A1 | 5/2018 | Kehry et al. |
| 2019/0276533 A1 | 9/2019 | Zhang et al. |
| 2019/0284280 A1 | 9/2019 | King et al. |
| 2019/0322746 A1 | 10/2019 | Bobilev et al. |
| 2020/0148770 A1 | 5/2020 | Kehry et al. |
| 2020/0164084 A1 | 5/2020 | Cortez et al. |
| 2022/0363759 A1 | 11/2022 | Kehry et al. |

FOREIGN PATENT DOCUMENTS

| | | |
|---|---|---|
| JP | 2005-523018 A | 8/2005 |
| WO | WO 1992/008796 | 5/1992 |
| WO | WO 1994/028143 | 12/1994 |
| WO | WO 2003/063792 | 8/2003 |
| WO | WO 2005/012524 | 2/2005 |
| WO | WO 2008/084261 | 7/2008 |
| WO | WO 2008/156712 | 12/2008 |
| WO | WO 2009/087381 | 7/2009 |
| WO | WO 2011/155607 | 12/2011 |
| WO | WO 2013/006490 | 1/2013 |
| WO | WO 2013/098420 | 7/2013 |
| WO | WO 2014/140240 | 9/2014 |
| WO | WO 2014/179664 | 11/2014 |
| WO | WO 2015/117002 | 8/2015 |
| WO | WO 2015/138920 | 9/2015 |
| WO | WO 2016/068802 | 5/2016 |
| WO | WO 2016/071448 | 5/2016 |
| WO | WO 2016/089888 | 6/2016 |
| WO | WO 2016/126858 | 9/2016 |
| WO | WO 2016/161270 | 10/2016 |
| WO | WO 2016/196726 | 12/2016 |
| WO | WO 2017/019894 | 11/2017 |
| WO | WO 2017/193032 | 11/2017 |
| WO | WO 2018/005818 | 1/2018 |
| WO | WO 2018/129553 | 7/2018 |

OTHER PUBLICATIONS

Bell et al., "Integrated genomic analyses of ovarian carcinoma," Cancer Genome Atlas Research Network, Nature, Jun. 29, 2011, 474(7353): 609-615.

Caldas et al., "Humanization of the anti-CD18 antibody 6.7: an unexpected effect of a framework residue in binding to antigen," Molecular Immunology, May 2003, 39(15): 941-952.

Casset et al., "A peptide mimetic of an anti-CD4 monoclonal antibody by rational design," Biochemical and Biophysical Research Communications, Jul. 18, 2003, 307(1): 198-205.

Chang et al., "Loop-Sequence Features and Stability Determinants in Antibody Variable Domains by High-Throughput Experiments," Structure, Jan. 7, 2014, 22(1): 9-21.

Chien et al., "Significant structural and functional change of an anti-gen-binding site by a distant amino acid substitution: Proposal of a structural mechanism," Proc. Natl. Acad. Sci. USA., Jul. 1989, 86(14): 5532-5536.

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology, 2002, 169(6): 3076-3084.

Giusti et al., "Somatic diversification of S107 from an antiphosphocholine to an anti-DNA autoantibody is due to a single base change in its heavy chain variable region," Proc. Natl. Acad. Sci. USA., May 1987, 84(9): 2926-2930.

Gussow et al., "[5] Humanization of Monoclonal Antibodies," Methods in Enzymology, 1991, 203: 99-121.

Holm et al., "Functional mapping and single chain construction of the anti-cytokeratin 8 monoclonal antibody TS1," Molecular Immunology, Feb. 2007, 44(6): 1075-1084.

Ingram et al., "Anti-CTLA-4 therapy requires an Fc domain for efficacy," Proc. Natl. Acad. Sci. USA., Apr. 10, 2018, 115(15): 3912-3917.

MacCallum et al., "Antibody-antigen Interactions: Contact Analysis and Binding Site Topography," J. Mol. Biol., Oct. 11, 1996, 262(5): 732-745.

Mariuzza et al., "The Structural Basis of Antigen-Antibody Recognition," Annual Review of Biophysics and Biophysical Chemistry, 1987, 16:139-159.

Nielsen et al., "Alternative splice variants of the human PD-1 gene," Cellular Immunology, Jun. 2005, 235(2): 109-116.

Rudikoff et al., "Single amino acid substitution altering antigen-binding specificity," Proc. Natl. Acad. Sci. USA., 1982, 79: 1979-1983.

Vajdos et al., "Comprehensive Functional Maps of the Antigen-binding Site of an Anti-ErbB2 Antibody Obtained with Shotgun Scanning Mutagenesis," J. Mol. Biol., Jul. 5, 2002, 320(2): 415-428.

Winkler et al., "Changing the Antigen Binding Specificity by Single Point Mutations of an Anti-p24 (HIV-1) Antibody," J. Immunol., Oct. 15, 2000, 165(8): 4505-4514.

Wu et al., "Humanization of a Murine Monoclonal Antibody by Simultaneous Optimization of Framework and CDR Residues," J. Mol. Biol., Nov. 19, 1999, 294(1): 151-162.

Yu et al., "Rationalization and Design of the Complementarity Determining Region Sequences in an Antibody-Antigen Recognition Interface," PLoS One, 2012, 7(3): e33340, pp. 1-15.

Altschul et al., "Basic local alignment search tool," J. Molecular Biol., 1990, 215(3):403-410.

Altschul et al., "Gapped BLAST and PSI-BLAST: a new generation of protein database search programs," Nucleic Acids Res., 1997, 25(17):3389-3402.

Anderson et al., "Promotion of tissue inflammation by the immune receptor Tim-3 expressed on innate immune cells," Science, 2007, 318:1141-1143.

Anderson et al., "TIM-3 in autoimmunity," Curr Opin Immunol., 2006, 18:665-669.

Anonymous: "View of NCT02608268 on Oct. 13, 2016", ClinicalTrials.gov Archive, Oct. 13, 2016 (Oct. 13, 2016), pp. 1-9, XP055458570, Retrieved from Internet: URL:https://clinicaltrials.gov/archive/NCT02608268/20161013 [retrieved on Mar. 12, 2018] the whole document.

Anonymous: "View of NCT02817633 on Jan. 14, 2016", ClinicalTrials.gov Archive, Nov. 14, 2016 (Nov. 14, 2016), pp. 1-7, XP055458594, Retrieved from Internet: URL: https://clinicaltrials.gov/archive/NCT02817633/2016_11_14 [retrieved on Mar. 12, 2018].

Ayers et al., "IFN-γ-related mRNA profile predicts clinical response to PD-1 blockade," J Clin Invest., 2017, 127(8):2930-2940, 2017.

Baitsch et al., "Extended Co-Expression of Inhibitory Receptors by Human CD8 T-Cells Depending on Differentiation, Antigen-Specificity and Anatomical Localization," PLoS ONE, 2012, 7:e30852.

Beigert et al., "Sequence context-specific profiles for homology searching," Proc. Natl. Acad Sci. USA, 2009, 106(10):3770-3775.

Bhatia et al., "Immunobiology of Merkel cell carcinoma: implications for immunotherapy of a polyomavirus-associated cancer," Curr Oncol Rep., 2011, 13(6):488-497.

Bird et al., "Single-chain antigen-binding proteins," Science, 1988, 242:423-426 (1988).

Blumberg et al., "IL-1RL2 and its ligands contribute to the cytokine network in psoriasis," J. Immunol., 2010, 185(7):4354-4362.

Blumberg et al., "Opposing activities of two novel members of the IL-1 ligand family regulate skin inflammation," J. Exp. Med., 2007, 204(11): 2603-2614.

Bohnsack et al., "Adaptaion of the immune-related response criteria: irRecist," ESMO, 2014, ABSTRACT 4958.

Bowers et al., "Coupling mammalian cell surface display with somatic hypermutation for the discovery and maturation of human antibodies," Proc. Natl. Acad. Sci. USA, 2011, 108(51):20455-20460.

(56) References Cited

OTHER PUBLICATIONS

Braitbard et al., "Competition between bound and free peptides in an ELISA-based procedure that assays peptides derived from protein digests," Proteome Science., 2006, 4(12):1-14.
Brash et al., "Strontium phosphate transfection of human cells in primary culture: stable expression of the simian virus 40 large-T-antigen gene in primary human bronchial epithelial cells," Mol. Cell Biol., 1987, 7:2031-2034.
Brown et al., "Tolerance to single, but not multiple, amino acid replacements in antibody V CDR2: a means of minimizing B cell wastage from somatic hypermutation?" J of Immunol., 1996, 156:3285-3291.
Burkhart et al., "Peptide-induced T cell regulation of experimental autoimmune encephalomyelitis: a role for IL-10," Int bnmunol., 1999, 11:1625-1634.
Chiba et al., "Tumor-infiltrating DCs suppress nucleic acid-mediated innate immune responses through interactions between the receptor TIM-3 and the alarmin HMGB1," Nature Immunology, 2012, 13: 832-842.
Clayton et al., "T Cell Ig and Mucin Domain-Containing Protein 3 Is Recruited to the Immune Synapse, Disrupts Stable Synapse Formation, and Associates with Receptor Phosphatases," J Immunol., 2014, 192(2):782-791.
ClinicalTrials.gov [online], "NCT02723955: Dose Escalation and Expansion Study of GSK3359609 in Participants With Selected Advanced Solid Tumors (INDUCE-1)," GlaxoSmithKline, Mar. 31, 2016, retrieved on Oct. 7, 2021, retrieved from URL <https://clinicaltrials.gov/ct2/show/NCT02723955>, 16 pages.
ClinicalTrials.gov [online], "NCT02817633: A Study of TSR-022 in Participants With Advanced Solid Tumors (AMBER)," Tesaro, Inc., Jun. 29, 2016, retrieved on Oct. 7, 2021, retrieved from URL <https://clinicaltrials.gov/ct2/show/NCT02817633>, 15 pages.
ClinicalTrials.gov [online], "NCT03680508: TSR-022 (Anti-TIM-3 Antibody) and TSR-042 (Anti-PD-1 Antibody) in Patients With Liver Cancer," University of Hawaii, Sep. 21, 2018, retrieved on Oct. 7, 2021, retrieved from URL <https://clinicaltrials.gov/ct2/show/NCT03680508>, 9 pages.
ClinicalTrials.gov [online], "NCT03739710: Platform Trial of Novel Regimens Versus Standard of Care (SoC) in Non-small Cell Lung Cancer (NSCLC)," GlaxoSmithKline, Nov. 14, 2018, retrieved on Oct. 7, 2021, retrieved from URL <https://clinicaltrials.gov/ct2/show/NCT03739710>, 14 pages.
ClinicalTrials.gov [online], "NCT04139902: Neoadjuvant PD-1 Inhibitor Dostarlimab (TSR-042) vs. Combination of Tim-3 Inhibitor Cobolimab (TSR-022) and PD-1 Inhibitor Dostarlimab (TSR-042) in Melanoma," Diwakar Davar, Oct. 25, 2019, retrieved on Oct. 7, 2021, retrieved from URL <https://clinicaltrials.gov/ct2/show/NCT04139902>, 10 pages.
ClinicalTrials.gov [online], "NCT04655976: Study of Cobolimab in Combination With Dostarlimab and Docetaxel in Advanced NSCLC Participants (COSTAR Lung)," GlaxoSmithKline, Dec. 7, 2020, retrieved on Oct. 7, 2021, retrieved from URL <https://clinicaltrials.gov/ct2/show/NCT04655976>, 10 pages.
Colbere-Garapin et al., "A new dominant hybrid selective marker for higher eukarvotic cells." J. Molecular Biol., 1981, 150(1):1-14.
Conese et al., "Gene therapy progress and prospects: episomally maintained self-replicating systems," Gene Therapy, 2004, 11:1735-1742.
Davar et al., "A Phase 1 Study of TSR-022 (Anti-TIM-3) in Combination with TSR-042 (Anti-PD-1)," Oral Presentation, Society for Immunotherapy of Cancer 33rd Annual Meeting, Nov. 7-11, 2018, 21 pages.
Davar et al., "A Phase 1 Study of TSR-022, an Anti-TIM-3 Monoclonal Antibody, in Combination with TSR-042 (Anti-PD-1) in Patients with Colorectal Cancer and Post-PD-1 NSCLC and Melanoma," Full Poster, Society for Immunotherapy of Cancer 33rd Annual Meeting, Nov. 7-11, 2018, 1 page.
Davar et al., "A phase 1 study of TSR-022, an anti-TIM-3 monoclonal antibody, in combination with TSR-042 (anti-PD-1) in patients with colorectal cancer and post-PD-1 NSCLC and melanoma," Submission Summary, Aug. 1, 2018, retrieved from URL <https://sitc.planion.com/Web.User/ProofForm?FT=ABSSUBMIT&ACCOUNT=SITC&FORMID=10361&SCHEDID=10877&CONF=RABS18&CKEY=15HH13HSS>, 3 pages.
David et al., "Protein iodination with solid state lactoperoxidase," Biochemistry, 1974, 13:1014-1021.
Davies et al. "Antibody-Antigen Complexes," Annual Rev Biochem., 1990, 59:439-473.
De Waal et al., "Pustulosis palmopiantaris is a disease distinct from psoriasis" J. Dermatoloaical Treatment, 2011, 22(2):102-105.
Deben et al., "APR-246 (PRIMA-1MET) strongly synergizes with AZD2281 (olaparib) induced PARP inhibition to induce apoptpsis in non-small cell lung cancer cell lines," Cancer Letters, 2016, 375(2):313-322.
DeKruyff et al., "T Cell/Transmembrane, Ig, and Mucin-3 Allelic Variants Differentially Recognize Phosphatidylserine and Mediate Phagocytosis of Apoptotic Cells," J Immunol., 2010, 184(4):1918-1930.
Dinarello et al., "IL-1 family nomenclature," Nat. Immunol., 2010, 11(11):973.
Eisenhauer, et al., "New response evaluation criteria in solid tumors: Revised RECIST guideline (version 1.1.)," Eur. J. of Cancer, 45: 228-247 (2009).
EP Search Report in European Appln. No. 17867255.6, dated Jul. 6, 2020, 10 pages.
EP Search Report in European Appln. No. 20150611.0, dated May 8, 2020, 10 pages.
European Patent Office, extended European Search Report in European Patent Application No. 16774301.2 (dated Nov. 14, 2018).
Fourcade et al., "Upregulation of Tim-3 and PD-1 expression is associated with tumor antigen-specific CD8+ T cell dysfunction in melanoma patients," J. Exp. Med., 2010, 207(10):2175-2186.
Fuhrmann-Benzakein et al., "Inducible and irreversible control of gene expression using a single transgene," Nuc. Acid. Res., 2000, 28:e99.
GenBank Accession No. AEX28953.1, "immunoglobulin G heavy chain variable region, partial [*Homo sapiens*]," Jan. 10, 2014, 2 pages.
Golden-Mason et al., "Negative Immune Regulator Tim-3 Is Overexpressed on T Cells in Hepatitis C Virus Infection and Its Blockade Rescues Dysfunctional CD4+ and CD8+ T Cells," J Virol., 2009, 83(18):9122-9130.
Guo et al., "Combined TIM-3 blockade and CD 137 activation affords the long-term protection in a murine model of ovarian cancer," Journal of Translational Medicine, 2013, 11:215.
Han et al., "Tim-3: an activation marker and activation limiter of innate immune cells," Frontiers in Immunology, 2013, 4:449.
Hastings et al., "TIM-3 is expressed on activated human CD4+ T cells and regulates Th1 and Th17 cytokines," Eur J Immunol., 2009, 39: 2492-2501.
Holliger et al., "Engineered antibody fragments and the rise of singie domains," Nature biotechnol., 2005, 23(9):1126-1136.
Horlick et al., "Combinatorial gene expression using multiple episomal vectors," Gene, 2000, 243(1-2):187-194.
Hou et al., "Humanization of an anti-CD34 monoclonal antibody by complementarity-determining region grafting based on computer-assisted molecular modelling," J. Biochem., 2008, 144(1):115-120.
Huang et al., "CEACAM1 regulates TIM-3-mediated tolerance and exhaustion," Nature, 2015, 517(7534):386-90.
Hunter et al., "Preparation of iodine-131 labelled human growth hormone of high specific activity," Nature, 1962, 194:495-496.
Huston et al., "Protein engineering of antibody binding sites: recovery of specific activity in an anti-digoxin single-chain Fv analogue produced in *Escherichia coli*," Proc. Natl. Acad. Sci. USA, 1988, 85:5879-5883.
Ichii et al., "Local overexpression of interleukin-1 family, member 6 relates to the development of tubulointerstitial lesions," Laboratory Investigation, 2010, 90(3):459-475.
Ignatova, "Monitoring protein stability in vivo," Microb. Cell Fact., 2005, 4:23.
Indra et al., "Temporally-controlled site-specific mutagenesis in the basal layer of the epidermis: comparison of the recombinase activity

(56) References Cited

OTHER PUBLICATIONS of the tamoxifen-inducible Cre-ER(T) and Cre-ER(T2) recombinases," Nuc. Acid. Res., 1999, 27:4324-4327.
International Preliminary Report on Patentability in International Appln. No. PCT/US2017/059619, dated May 7, 2019, 7 pages.
International Search Report and Written Opinion in International Application No. PCT/US2016/025532 (dated Aug. 22, 2016).
International Search Report and Written Opinion in International Application No. PCT/US2017/059619 (dated Jun. 15, 2018).
International Search Report and Written Opinion in International Appln. No. PCT/US2016/025535, dated Aug. 22, 2016, 16 pages.
International Search Report and Written Opinion in International Appln. No. PCT/US2017/059619, dated Jun. 15, 2018, 10 pages.
International Search Report in International Appln. No. PCT/US2018/013021, dated Mar. 23, 2018, 6 pages.
Jack et al., "Looping out and deletion mechanism for the immunoglobulin heavy-chain class switch," Proc. Natl. Acad. Sci. USA, 1988, 85:1581-1585.
Jin et al., "Cooperation of Tim-3 and PD-1 in CD8 T-cell exhaustion during chronic viral infection," Proc Natl Acad Sci USA, 2010, 107(33):14733-14738.
Johnston, "Biolistic transformation: microbes to mice," Nature, 1990, 346:776-777.
Jones et al., "Tim-3 expression defines a novel population of dysfunctional T cells with highly elevated frequencies in progressive HIV-1 infection," J. Exp. Med., 2008, 205:2763-2779.
Ju et al., "T cell immunoglobulin- and mucin-domain-containing molecule-3 (Tim-3) mediates natural killer cell suppression in chronic hepatitis B," B. J. Hepatol., 2010, 52:322-329.
Kane, "TIM Proteins and Immunity," Journal of Immunology, 2010, 184(6):2743-2749.
Kashmiri et al., "SDR grafting—a new approach to antibody humanization," Methods, 2005, 36(1):25-34.
Kehry et al., "Targeting PD-1, TIM-3 and LAG-3 in Combination for Improved Immunotherapy Combinations," Poster, AACR Annual Meeting, 2015, 1 page.
Kent et al., "Ouabain resistance conferred by expression of the cDNA for a murine Na+, K+-ATPase alpha subunit," Science, 1987, 237:901-903.
Kitts et al., "A method for producing recombinant baculovirus expression vectors at high frequency," Biotechniques, 1993, 14:810-17.
Kohler and Milstein, "Derivation of specific antibody-producing tissue culture and tumor lines by cell fusion," Eur. J. Immunol., 1976, 5:511-519.
Kramer & Fussenegger, "Transgene control engineering in mammalian cells," Methods Mol. Biol., 2005, 308:123-144.
Kunik et al., "Structural Consensus among Antibodies Defines the Antigen Binding Site," PLoS Comutational Biology, Feb. 2012, 8(2):e1002388, 12 pages.
Le et al., "PD-1 Blockade in Tumors with Mismatch-Repair Deficiency," N. Engl. J. Med., 2015, 372(26):2509-2520.
Liberal et al., "The impaired immune regulation of autoimmune hepatitis is linked to a defective galectin-9/tim-3 pathway," Hepatology, 2012, 56(2):677-686.
Lonberg, "Human antibodies from transgenic animals," Nat. Biotechnol., 2005, 23(9):1117-25.
Lonberg, "Human monoclonal antibodies from transgenic mice," Handb. Exp. Pharmacol., 2008, 181:69-97.
Lowy et al., "Isolation of transforming DNA: cloning the hamster aprt gene," Cell, 1980, 22:817-823.
Lucklow et al., "Efficient generation of infectious recombinant baculoviruses by site-specific transposon-mediated insertion of foreign genes into a baculovims genome propagated in *Escherichia coli*," J Viral., 1993, 67:4566-4579.
Lucklow, "Baculovirus systems for the expression of human gene products," Curr. Opin. Biotechnol., 1993, 4:564-572.
Marrakchi et al., "Interleukin-36-receptor antagonist deficiency and generalized pustular psoriasis," N. Engl. J. Med., 2011, 365(7): 620-628.
McMahan et al., "Tim-3 expression on PD-1+ HCV-specific human CTLs is associated with viral persistence, and its blockade restores hepatocyte-directed in vitro cytotoxicity," J. Clin. Invest., 2010, 120(12):4546-4557.
Monney et al., "Th1-specific cell surface protein Tim-3 regulates macrophage activation and severity of an autoimmune disease," Nature, 2002, 415: 536-541.
Mulligan & Berg, "Selection for animal cells that express the *Escherichia coli* gene coding for xanthine-guanine phosphoribosyltransferase," Proc. Natl. Acad Sci. USA, 1981, 78:2072-2076.
Murtaza A et al: "Discovery of TRS-022, a Novel, Potent Anti-Human TIM-3 Therapeutic Antibody", European Journal of Cancer, vol. 69, 311, Nov. 29, 2016 (Nov. 29, 2016), p. S102.
Murtaza et al., "Discovery of TSR-022, a novel, potent anti-human TIM-3 therapeutic antibody," Poster Sessions: Immunotherapy, Nov. 29, 2016, Poster P137, 1 page.
Myers and Miller, "Optimal alignments in linear space," CABIOS, 1989, 4:11-17.
Naik et al., "Autoinflammatory pustular neutrophilic diseases," Dermatologic Clinics, 2013, 31(3):405-425.
Nakayama et al., "Tim-3 mediates phagocytosis of apoptotic cells and cross-presentation," Blood, 2009, 113:3821-3830.
Ndhlovu et al., "Tim-3 marks human natural killer cell maturation and suppresses cell-mediated cytotoxicity," Blood, 2012, 119:3734-3743.
Ngiow et al., "Anti-TIM3 antibody promotes T cell IFN-γ-mediated antitumor immunity and suppresses established tumors," Cancer Res., 2011, 71(10):3540-3551.
Ngiow et al., "Prospects for TIM3-Targeted Antitumor Immunotherapy," Cancer Res., 2011, 71(21):6567-6571.
Nishina et al., "Developing a common language for tumor response to immunotherapy: immune-related response criteria using unidimensional measurements," Clin. Cancer Res., 2013, 19(14):3936-43.
No et al., "Ecdysone-Inducible Gene Expression in Mammalian Cells and Transgenic Mice," Proc. Natl. Acad. Sci., 1996, 93:3346-3351.
Nygren, "Conjugation of horseradish peroxidase to Fab fragments with different homobifunctional and heterobifunctional cross-linking reagents. A comparative study," J Histochem. and Cytochem., 1982, 30:407-412.
O'Hare et al., "Transformation of mouse fibroblasts to methotrexate resistance by a recombinant plasmid expressing a prokaryotic dihydrofolate reductase," Proc. Natl. Acad Sci. USA, 1981, 78:1527-1531.
Osbourn et al., "Directed selection of MIP-1 alpha neutralizing CCR5 antibodies from a phage display human antibody library," Nat. Biotechnol., 1998, 16:778.
Pain et al., "Preparation of protein A-peroxidase monoconjugate using a heterobifunctional reagent, and its use in enzyme immunoassays," J Immunol. Meth., 1981, 40:219-230.
Rustin et al., "Definitions for response and progression in ovarian cancer clinical trials incorporating RECIST 1.1 and CA 125 agreed by the Gynecological Cancer Intergroup (GCIG)," Int J Gynecol Cancer 2011, 21:419-423.
Sakuishi et al., "Emerging Tim-3 functions in antimicrobial and tumor immunity," Trends in Immunology, 2011, 32(8): 345-349.
Sakuishi et al., "Targeting Tim-3 and PD-1 pathways to reverse T cell exhaustion and restore anti-tumor immunity," J. Exp. Med., 2010, 207(10):2187-2194.
Santerre et al., "Expression of prokaryotic genes for hygromycin B and G418 resistance as dominant-selection markers in mouse L cells," Gene, 1984, 30:147-156.
Seki et al., "Galectin-9 suppresses the generation of Th17, promotes the induction of regulatory T cells, and regulates experimental autoimmune arthritis ," Clin. Immunol., 2008, 127:78-88.
Sharma et al., "Evaluation of TSR-042, TSR-022 and TSR-033 as single agents and in combination in humanized mice," Poster, Regeneron's Workshop on Humanized Immune System (HIS) Mice, Nov. 28-30, 2018, 1 page.
Silva et al., "The S228P mutation prevents in vivo and in vitro IgG4 Fab-arm exchange as demonstrated using a combination of novel

(56) References Cited

OTHER PUBLICATIONS quantitative immunoassays and physiological matrix preparation," J. Biol. Chem. 2015, 290(9):5462-5469.
Soding, "Protein homology detection by HMM-HMM comparison," Bioinformatics, 2005, 21(7):951-960.
Sugiura et al., "The majority of generalized pustular psoriasis without psoriasis vulgaris is caused by deficiency of interleukin-36 receptor antagonist," J. Invest. Derm., 2013, 133(11):2514-2521.
Szybalska & Szybalski, "Genetics of human cell line. IV. DNA-mediated heritable transformation of a biochemical trait," Proc. Natl. Acad Sci. USA, 1962, 48:2026-2034.
Tortola et al., "Psoriasiform dermatitis is driven by IL-36-mediated DC-keratinocyte crosstalk," J. Clin. Invest., 2012, 122(11): 3965-3976.
Towne et al., "IL-36 in psoriasis," Curr. Opin. Pharmacol., 2012, 12(4):486-490.
Towne et al., "Interleukin (IL)-1 F6, IL-1 F8, and IL-1 F9 Signal through IL-1 Rrp2 and IL-1 RAcP to Activate the Pathway Leading to NF-kB and MAPKs" J. Biol. Chem., 2004, 279(14):13677-13688.
Turnis et al., "Combinatorial Immunotherapy: PD-1 may not be LAG-ing behind anymore," Oncoimmunology, 1.7, 2012, 1172-1174.
Urlaub et al., "Isolation of Chinese hamster cell mutants deficient in dihydrofolate reductase activity," Proc. Natl. Acad. Sci. USA, 1980, 97:4216-4220.
Vigne et al., "IL-36 signaling amplifies Th1 responses by enhancing proliferation and Th1 polarization of naive CD4+ T cells," Blood, 2012, 120(17):3478-3487.
Vigne et al., "IL-36R ligands are potent regulators of dendritic and T cells," Blood, 2011, 118(22):5813-5823.
Weiss et al., "A phase 1 study of TSR-022, an anti-TIM-3 monoclonal antibody, in patients (pts) with advanced solid tumors," Regular Abstract, SITC 32nd Annual meeting & Pre-Conference Programs, Aug. 1, 2017, 9 pages.
Weiss et al., "A Phase 1 Study of TSR-022, an Anti-TIM-3 Monoclonal Antibody, in Patients with Advanced Solid Tumors," Oral Presentation, Society for Immunotherapy of Cancer, Nov. 8-12, 2017, 12 pages.
Weiss et al., "A Phase 1 Study of TSR-022, an Anti-TIM-3 Monoclonal Antibody, in Patents (pts) With Advanced Solid Tumors," J. Immunothera. Cancer, 2017, 5(2):7.
Westdorp et al., "Opportunities for immunotherapy in microsatellite instable colorectal cancer," Cancer Immunol. Immunother., 2016, 65(10):1249-1259.
Wigler et al., "Transfer of purified herpes virus thymidine kinase gene to cultured mouse cells," Cell, 1977, 11:223-232.
Wigler et al., "Transformation of mammalian cells with an amplifiable dominant-acting gene," Proc. Natl. Acad Sci. USA, 1980, 77:3567-3570.
Woo et al., "Immune inhibitory molecules LAG-3 and PD-1 synergistically regulate T-cell function to promote tumoral immune escape," Cancer Res., 2012, 72:917-927.
Wu et al., "Blockade of Tim-3 signaling restores the virus-specific CD8+ T-cell response inpatients with chronic hepatitis B," Eur. J Immunol., 2012, 42(5):1180-1191.
Zahra et al., "Randomized Phase II Neoadjuvant Study of PD-1 Inhibitor Dostarlimab (TSR-042) vs. Combination of Tim-3 Inhibitor TSR-022 and PD-1 Inhibitor Dostarlimab (TSR-042) in Resectable Stage III or Oligometastatic Stage IV Melanoma (Neo-MEL-T)," Society for Immunotherapy of Cancer—34th Annual Meeting, Nov. 6-10, 2019, P457, 1 page.
Zhou et al., "Coexpression of Tim-3 and PD-1 identifies a CD8+ T-cell exhaustion phenotype in mice with disseminated acute myelogenous leukemia," Blood, 2011, 117(17):4501-4510.
Zhu et al., "The Tim-3 ligand galectin-9 negatively regulates T helper type 1 immunity ," Nat. Immunol., 2005, 6:1245-1252.
U.S. Appl. No. 15/563,924, filed Oct. 2, 2017, Marilyn Kehry.
U.S. Appl. No. 16/400,165, filed May 1, 2019, Marilyn Kehry.
U.S. Appl. No. 16/655,939, filed Oct. 17, 2019, Marilyn Kehry.
U.S. Appl. No. 16/476,534, filed Jul. 8, 2019, Dmitri Bobilev.
ABCD_AA805 in the ABCD (AntiBodies Chemically Defined) Database, retrieved on Oct. 18, 2022, retrieved from URL<https://web.expasy.org/abcd/ABCD_AA805>, 1 page.
Acharya et al., "Tim-3 finds its place in the cancer immunotherapy landscape," Journal for ImmunoTherapy of Cancer, Jun. 2020, 8(1): e000911.
Acoba et al., "Phase II study of cobolimab in combination with dostarlimab for the treatment of advanced hepatocellular carcinoma.," J. Clin. Oncol., Feb. 1, 2023, 41 (4 Suppl.):580.
Anderson et al., "Tim-3: an emerging target in the cancer immunotherapy landscape," Cancer Immunol Res., May 2014, 2(4):393-8.
Anderson, "Tim-3, a negative regulator of anti-tumor immunity," Current Opinion in Immunology, Apr. 2012, 24(2):213-216.
Bailly et al., "Soluble TIM-3 as a biomarker of progression and therapeutic response in cancers and other of human diseases," Biochemical Pharmacology, Mar. 2023, 209: 115445.
Cemiplimab, Statement On a Nonproprietary Name Adopted By the USAN Council, retrieved on Oct. 18, 2022, retrieved from URL<https://searchusan.ama-assn.org/usan/documentDownload?uri=%2Funstructured%2Fbinary%2Fusan%2Fcemiplimab.pdf>, 2 pages.
Chen et al., "Generation and analysis of random point mutations in an antibody CDR2 sequence: many mutated antibodies lose their ability to bind antigen," Sep. 1992, J. Exp. Med. 176:855-66.
Chunmei et al., "Biological activity and application of TIM-3 antibody," Military Medical Sciences, 2014, 8:617-625 (Abstract Only).
clinicaltrials.gov [online], "NCT02608268: Phase I-Ib/II Study of MBG453 as Single Agent and in Combination With PDR001 in Patients With Advanced Malignancies," Nov. 18, 2015, retrieved on Jan. 17, 2023, retrieved from URL<https://clinicaltrials.gov/ct2/show/NCT02608268?term=nct02608268&draw=2&rank=1>, 10 pages.
ClinicalTrials.gov [online], "NCT03307785: Study of Niraparib, TSR-022, Bevacizumab, and Platinum-Based Doublet Chemotherapy in Combination With TSR-042," Oct. 12, 2017, retrieved on Mar. 23, 2023, retrieved from URL < https://clinicaltrials.gov/ct2/show/NCT03307785>, 52 pages.
Dostarlimab, Statement On a Nonproprietary Name Adopted By the USAN Council, retrieved on Oct. 17, 2022, retrieved from URL<https://searchusan.ama-assn.org/usan/documentDownload?uri=%2Funstructured%2Fbinary%2Fusan%2Fdos tarlimab.pdf>, 2 pages.
Falchook et al., "Phase 1 trial of TIM-3 inhibitor cobolimab monotherapy and in combination with PD-1 inhibitors nivolumab or dostarlimab (AMBER)," Journal of Clinical Oncology, Feb. 1, 2023, 41(4 Suppl.):580.
Finlay et al., "Anti-PD1 'SHR-1210' aberrantly targets pro-angiogenic receptors and this polyspecificity can be ablated by paratope refinement," 2019, MABS, vol. 11, No. 1, 26-44.
Gomes de Morais et al., "New Checkpoint Inhibitors on the Road: Targeting TIM-3 in Solid Tumors," Current Oncology Reports, May 2022, 24(5):651-658.
Harding et al., "Blocking TIM-3 in Treatment-refractory Advanced Solid Tumors: A Phase Ia/b Study of LY3321367 with or without any Anti-PD-L1 Antibody," Clinical Cancer Research, Apr. 15, 2021, 27(8): 2168-2178.
Hollebecque et al., "Safety and Antitumor Activity of α-PD-L1 Antibody as Monotherapy or in Combination with α-TIM-3 Antibody in Patients with Microsatellite Instability-High/Mismatch Repair-Deficient Tumors," Clinical Cancer Research, Dec. 1, 2021, 27(23):6393-6404.
Kegg Drug: Nivolumab, retrieved on Oct. 17, 2022, retrieved from URL<https://www.genome.jp/dbget-bin/www bget?drug:D10316>, 2 pages.
Kim et al., "Combination Therapy with Anti-PD-1, Anti-TIM-3, and Focal Radiation Results in Regression of Murine Gliomas," Clinical Cancer Research, Jan. 1, 2017, 23(1):124-136.
Klein et al., "Somatic Mutations of the Immunoglobulin Framework Are Generally Required for Broad and Potent HIV-1 Neutralization," Mar. 2013, Cell, vol. 153, Issue 1, pp. 126-138.
Liu et al., "Targeting PD-1 and Tim-3 Pathways to Reverse CD8 T-Cell Exhaustion and Enhance Ex Vivo T-Cell Responses to Autologous Dendritic/Tumor Vaccines," J Immunother., May 2016, 39(4): 171-80.

(56) References Cited

OTHER PUBLICATIONS

Malmqvist, "Biospecific interaction analysis using biosensor technology," Nature, Jan. 14, 1993, 361:186-187.

Mathijssen et al., "Flat-Fixed Dosing Versus Body Surface Area-Based Dosing of Anticancer Drugs in Adults: Does It Make a Difference?" The Oncologist, Aug. 2007, 12(8): 913-923.

Nivolumab, Statement On a Nonproprietary Name Adopted By the USAN Council, retrieved on Oct. 17, 2022, retrieved from URL<https://searchusan.ama-assn.org/usan/documentDownload?uri=/unstructured/binary/usan/nivolumab.pdf>, 1 page.

Pembrolizumab, Statement On a Nonproprietary Name Adopted By the USAN Council, Nov. 27, 2013, retrieved on Oct. 17, 2022, retrieved from URL<https://searchusan.ama-assn.org/usan/documentDownload?uri=%2Funstructured%2Fbinary%2Fusan%2Fpembrolizumab.pdf>, 2 pages.

Sun et al., "Dual but not single PD-1 or TIM-3 blockade enhances oncolytic virotherapy in refractory lung cancer," J. Immunother. Cancer, May 2020, 8(1):e000294, 12 pages.

Takashima et al., "Differential expression of individual transcript variants of PD-1 and PD-L2 genes on Th-1/Th-2 status is guaranteed for prognosis prediction in PCNSL," Scientific Reports, Jul. 10, 2019, 9(1):10004.

Tislelizumab, Statement On a Nonproprietary Name Adopted By the USAN Council, retrieved on Oct. 17, 2022, retrieved from URL<https://searchusan.ama-assn.org/usan/documentDownload?uri=%2Funstructured%2Fbinary%2Fusan%2Ftislelizumab.pdf>, 2 pages.

Yap et al., "IOLite: phase 1b trial of doublet/triplet combinations of dostarlimab with niraparib, carboplatin-paclitaxel, with or without bevacizumab in patients with advanced cancer," Journal for Immuno Therapy of Cancer, Mar. 2022, 10(3):e003924.

\* cited by examiner

```
                        SEQUENCE LISTING

<160> NUMBER OF SEQ ID NOS: 19

<210> SEQ ID NO 1
    <211> LENGTH: 440
    <212> TYPE: PRT
    <213> ORGANISM: Artificial
    <220> FEATURE:
    <223> OTHER INFORMATION: Synthetic heavy chain polypeptide that can bind
          a TIM-3 polypeptide

<400> SEQUENCE: 1

Glu Val Gln Leu Leu Glu Ser Gly Gly Gly Leu Val Gln Pro Gly Gly
    1               5                   10                  15

Ser Leu Arg Leu Ser Cys Ala Ala Ser Gly Phe Thr Phe Ser Ser
                20                  25                  30

Tyr Asp Met Ser Trp Val Arg Gln Ala Pro Gly Lys Gly Leu Asp Trp
                35                  40                  45

Val Ser Thr Ile Ser Gly Gly Gly Thr Tyr Thr Tyr Tyr Gln Asp Ser
        50                  55                  60

Val Lys Gly Arg Phe Thr Ile Ser Arg Asp Asn Ser Lys Asn Thr Leu
    65                  70                  75                  80

Tyr Leu Gln Met Asn Ser Leu Arg Ala Glu Asp Thr Ala Val Tyr Tyr
                    85                  90                  95

Cys Ala Ser Met Asp Tyr Trp Gly Gln Gly Thr Thr Val Thr Val Ser
                    100                 105                 110

Ser Ala Ser Thr Lys Gly Pro Ser Val Phe Pro Leu Ala Pro Cys Ser
                115                 120                 125

Arg Ser Thr Ser Glu Ser Thr Ala Ala Leu Gly Cys Leu Val Lys Asp
            130                 135                 140

Tyr Phe Pro Glu Pro Val Thr Val Ser Trp Asn Ser Gly Ala Leu Thr
    145                 150                 155                 160

Ser Gly Val His Thr Phe Pro Ala Val Leu Gln Ser Ser Gly Leu Tyr
                    165                 170                 175

Ser Leu Ser Ser Val Val Thr Val Pro Ser Ser Ser Leu Gly Thr Lys
                    180                 185                 190

Thr Tyr Thr Cys Asn Val Asp His Lys Pro Ser Asn Thr Lys Val Asp
                195                 200                 205

Lys Arg Val Glu Ser Lys Tyr Gly Pro Pro Cys Pro Pro Cys Pro Ala
            210                 215                 220

Pro Glu Phe Leu Gly Gly Pro Ser Val Phe Leu Phe Pro Pro Lys Pro
    225                 230                 235                 240

Lys Asp Thr Leu Met Ile Ser Arg Thr Pro Glu Val Thr Cys Val Val
                    245                 250                 255

Val Asp Val Ser Gln Glu Asp Pro Glu Val Gln Phe Asn Trp Tyr Val
                    260                 265                 270

Asp Gly Val Glu Val His Asn Ala Lys Thr Lys Pro Arg Glu Glu Gln
                275                 280                 285
```

```
Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
                340                 345                 350

Lys Asn Gln Val Ser Leu Thr Cys Leu Val Lys Gly Phe Tyr Pro Ser
                355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys
                435                 440

<210> SEQ ID NO 2
<211> LENGTH: 214
<212> TYPE: PRT
<213> ORGANISM: Artificial
<220> FEATURE:
<223> OTHER INFORMATION: Synthetic light chain polypeptide that can bind
      a TIM-3 polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Arg Tyr
                20                  25                  30

Leu Asn Trp Tyr His Gln Lys Pro Gly Lys Ala Pro Lys Leu Leu Ile
            35                  40                  45

Tyr Gly Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Ser His Ser Ala Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
```

Phe Asn Arg Gly Glu Cys
    210

<210> SEQ ID NO 3
<211> LENGTH: 1320
<212> TYPE: DNA
<213> ORGANISM: Artificial
<220> FEATURE:
<223> OTHER INFORMATION: Synthetic polynucleotide encoding a heavy chain
      polypeptide that can bind a TIM-3 polypeptide

<400> SEQUENCE: 3

| | | | | | |
|---|---|---|---|---|---|
| gaggtgcagc | tgttggagtc | tgggggaggc | ttggtacagc | ctggggggtc | cctgagactc | 60 |
| tcctgtgcag | cagcctctgg | attcactttc | agtagctatg | acatgtcttg | ggtccgccag | 120 |
| gctccaggga | aggggctgga | ctgggtctca | accattagtg | gtggtggtac | ttacacctac | 180 |
| tatcaagaca | gtgtgaaggg | gcggttcacc | atctccagag | acaattccaa | gaacacgctg | 240 |
| tatctgcaaa | tgaacagcct | gagagccgag | gacacggccg | tatattactg | tgcgtccatg | 300 |
| gactactggg | gcaagggac | cacggtcacc | gtctcctcag | catccaccaa | gggcccatcg | 360 |
| gtcttccccgc | tagcaccctg | ctccaggagc | acctccgaga | gcacagccgc | cctgggctgc | 420 |
| ctggtcaagg | actacttccc | cgaaccagtg | acggtgtcgt | ggaactcagg | cgccctgacc | 480 |
| agcggcgtgc | acaccttccc | ggctgtccta | cagtcctcag | gactctactc | cctcagcagc | 540 |
| gtggtgaccg | tgccctccag | cagcttgggc | acgaagacct | acacctgcaa | cgtagatcac | 600 |
| aagcccagca | acaccaaggt | ggacaagaga | gttgagtcca | aatatggtcc | cccatgccca | 660 |
| ccatgcccag | cacctgagtt | cctggggggga | ccatcagtct | tcctgttccc | cccaaaaccc | 720 |
| aaggacactc | tcatgatctc | ccggacccct | gaggtcacgt | gcgtggtggt | ggacgtgagc | 780 |
| caggaagacc | ccgaggtcca | gttcaactgg | tacgtggatg | gcgtggaggt | gcataatgcc | 840 |
| aagacaaagc | cgcgggagga | gcagttcaac | agcacgtacc | gtgtggtcag | cgtcctcacc | 900 |
| gtcctgcacc | aggactggct | gaacggcaag | gagtacaagt | gcaaggtctc | caacaaaggc | 960 |
| ctcccgtcct | ccatcgagaa | aaccatctcc | aaagccaaag | gcagccccg | agagccacag | 1020 |
| gtgtacaccc | tgcccccatc | ccaggaggag | atgaccaaga | accaggtcag | cctgacctgc | 1080 |
| ctggtcaaag | gcttctaccc | cagcgacatc | gccgtggagt | gggagagcaa | tgggcagccg | 1140 |
| gagaacaact | acaagaccac | gcctcccgtg | ctggactccg | acggctcctt | cttcctctac | 1200 |
| agcaggctaa | ccgtggacaa | gagcaggtgg | caggagggga | atgtcttctc | atgctccgtg | 1260 |
| atgcatgagg | ctctgcacaa | ccactacaca | cagaagagcc | tctccctgtc | tctgggtaaa | 1320 |

<210> SEQ ID NO 4
<211> LENGTH: 642
<212> TYPE: DNA
<213> ORGANISM: Artificial
<220> FEATURE:
<223> OTHER INFORMATION: Synthetic polynucleotide encoding a light chain
      polypeptide that can bind a TIM-3 polypeptide

<400> SEQUENCE: 4

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gagcattagg | aggtatttaa | attggtatca | gcagaaacca | 120 |
| gggaaagccc | ctaagctcct | gatctatggt | gcatccacct | tgcaaagtgg | ggtcccatca | 180 |
| aggttcagtg | gtagtggatc | tgggacagat | ttcactctca | ccatcagcag | tctgcaacct | 240 |

```
gaagattttg cagtgtatta ctgtcaacag agtcacagtg ccccctcac tttcggcgga    300 gggaccaagg tggagatcaa acgaactgtg gctgcaccat ctgtcttcat cttcccgcca    360
tctgatgagc aattgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga aaacacaaa gtctacgcct gcgaagtcac ccatcagggc    600
ctcagctcgc ccgtcacaaa gagcttcaac aggggagagt gt    642
```

<210> SEQ ID NO 5
<211> LENGTH: 459
<212> TYPE: PRT
<213> ORGANISM: Artificial
<220> FEATURE:
<223> OTHER INFORMATION: Synthetic heavy chain polypeptide including a signal peptide that can bind a TIM-3 polypeptide

<400> SEQUENCE: 5

```
Met Glu Phe Gly Leu Ser Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ala Ala Ala Ser Gly Phe Thr
        35                  40                  45

Phe Ser Ser Tyr Asp Met Ser Trp Val Arg Gln Ala Pro Gly Lys Gly
    50                  55                  60

Leu Asp Trp Val Ser Thr Ile Ser Gly Gly Gly Thr Tyr Thr Tyr Tyr
65                  70                  75                  80

Gln Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Ser Met Asp Tyr Trp Gly Gln Gly Thr Thr Val
        115                 120                 125

Thr Val Ser Ser Ala Ser Thr Lys Gly Pro Ser Val Phe Pro Leu Ala
    130                 135                 140

Pro Cys Ser Arg Ser Thr Ser Glu Ser Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Lys Thr Tyr Thr Cys Asn Val Asp His Lys Pro Ser Asn Thr
    210                 215                 220

Lys Val Asp Lys Arg Val Glu Ser Lys Tyr Gly Pro Pro Cys Pro Pro
225                 230                 235                 240

Cys Pro Ala Pro Glu Phe Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Glu Asp Pro Glu Val Gln Phe Asn
        275                 280                 285
```

```
Trp Tyr Val Asp Gly Val Glu Val His Asn Ala Lys Thr Lys Pro Arg
            290                 295                 300

Glu Glu Gln Phe Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
            325                 330                 335

Asn Lys Gly Leu Pro Ser Ser Ile Glu Lys Thr Ile Ser Lys Ala Lys
            340                 345                 350

Gly Gln Pro Arg Glu Pro Gln Val Tyr Thr Leu Pro Pro Ser Gln Glu
            355                 360                 365

Glu Met Thr Lys Asn Gln Val Ser Leu Thr Cys Leu Val Lys Gly Phe
370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
            405                 410                 415

Phe Leu Tyr Ser Arg Leu Thr Val Asp Lys Ser Arg Trp Gln Glu Gly
            420                 425                 430

Asn Val Phe Ser Cys Ser Val Met His Glu Ala Leu His Asn His Tyr
            435                 440                 445

Thr Gln Lys Ser Leu Ser Leu Ser Leu Gly Lys
    450                 455

<210> SEQ ID NO 6
<211> LENGTH: 236
<212> TYPE: PRT
<213> ORGANISM: Artificial
<220> FEATURE:
<223> OTHER INFORMATION: Synthetic light chain polypeptide including a
      signal peptide that can bind a TIM-3 polypeptide

<400> SEQUENCE: 6

Met Asp Met Arg Val Pro Ala Gln Leu Leu Gly Leu Leu Leu Leu Trp
1               5                   10                  15

Leu Arg Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Ser Ile Arg Arg Tyr Leu Asn Trp Tyr His Gln Lys Pro Gly Lys
    50                  55                  60

Ala Pro Lys Leu Leu Ile Tyr Gly Ala Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Val Tyr Tyr Cys Gln Gln
            100                 105                 110

Ser His Ser Ala Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190
```

```
Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 7
<211> LENGTH: 28
<212> TYPE: PRT
<213> ORGANISM: Artificial
<220> FEATURE:
<223> OTHER INFORMATION: Disulfide-containing peptide

<400> SEQUENCE: 7

Val Thr Ile Thr Cys Arg Phe Ser Gly Ser Gly Ser Gly Thr Asp Phe
1               5                   10                  15

Thr Leu Thr Ile Ser Ser Leu Gln Pro Glu Asp Phe
            20                  25

<210> SEQ ID NO 8
<211> LENGTH: 20
<212> TYPE: PRT
<213> ORGANISM: Artificial
<220> FEATURE:
<223> OTHER INFORMATION: Disulfide-containing peptide

<400> SEQUENCE: 8

Ala Val Tyr Tyr Cys Gln Gln Ser His Ser Ala Pro Leu Thr Phe Gly
1               5                   10                  15

Gly Gly Thr Lys
            20

<210> SEQ ID NO 9
<211> LENGTH: 33
<212> TYPE: PRT
<213> ORGANISM: Artificial
<220> FEATURE:
<223> OTHER INFORMATION: Disulfide-containing peptide

<400> SEQUENCE: 9

Ser Gly Thr Ala Ser Val Val Cys Leu Leu Asn Asn Phe Tyr Pro Arg
1               5                   10                  15

Val Tyr Ala Cys Glu Val Thr His Gln Gly Leu Ser Ser Pro Val Thr
            20                  25                  30

Lys

<210> SEQ ID NO 10
<211> LENGTH: 19
<212> TYPE: PRT
<213> ORGANISM: Artificial
<220> FEATURE:
<223> OTHER INFORMATION: Disulfide-containing peptide

<400> SEQUENCE: 10

Ser Phe Asn Arg Gly Glu Cys Gly Pro Ser Val Phe Pro Leu Ala Pro
1               5                   10                  15

Cys Ser Arg

<210> SEQ ID NO 11
<211> LENGTH: 15
<212> TYPE: PRT
```

<213> ORGANISM: Artificial
<220> FEATURE:
<223> OTHER INFORMATION: Disulfide-containing peptide

<400> SEQUENCE: 11

Gly Glu Cys Gly Pro Ser Val Phe Pro Leu Ala Pro Cys Ser Arg
1               5                   10                  15

<210> SEQ ID NO 12
<211> LENGTH: 25
<212> TYPE: PRT
<213> ORGANISM: Artificial
<220> FEATURE:
<223> OTHER INFORMATION: Disulfide-containing peptide

<400> SEQUENCE: 12

Leu Ser Cys Ala Ala Ala Ser Gly Phe Thr Phe Ser Ser Tyr Asp Met
1               5                   10                  15

Ser Trp Val Arg Ala Glu Asp Thr Ala
            20                  25

<210> SEQ ID NO 13
<211> LENGTH: 24
<212> TYPE: PRT
<213> ORGANISM: Artificial
<220> FEATURE:
<223> OTHER INFORMATION: Disulfide-containing peptide

<400> SEQUENCE: 13

Val Tyr Tyr Cys Ala Ser Met Asp Tyr Trp Gly Gln Gly Thr Thr Val
1               5                   10                  15

Thr Val Ser Ser Ala Ser Thr Lys
            20

<210> SEQ ID NO 14
<211> LENGTH: 23
<212> TYPE: PRT
<213> ORGANISM: Artificial
<220> FEATURE:
<223> OTHER INFORMATION: Disulfide-containing peptide

<400> SEQUENCE: 14

Ser Thr Ser Glu Ser Thr Ala Ala Leu Gly Cys Leu Val Lys Thr Tyr
1               5                   10                  15

Thr Cys Asn Val Asp His Lys
            20

<210> SEQ ID NO 15
<211> LENGTH: 28
<212> TYPE: PRT
<213> ORGANISM: Artificial
<220> FEATURE:
<223> OTHER INFORMATION: Disulfide-containing peptide

<400> SEQUENCE: 15

Ser Thr Ser Glu Ser Thr Ala Ala Leu Gly Cys Leu Val Lys Thr Tyr
1               5                   10                  15

Thr Cys Asn Val Asp His Lys Pro Ser Asn Thr Lys
            20                  25

<210> SEQ ID NO 16
<211> LENGTH: 50
<212> TYPE: PRT
<213> ORGANISM: Artificial
<220> FEATURE:

```
<223> OTHER INFORMATION: Disulfide-containing peptide

<400> SEQUENCE: 16

Tyr Gly Pro Pro Cys Pro Pro Cys Pro Ala Pro Glu Phe Leu Gly Gly
1               5                   10                  15

Pro Ser Val Phe Leu Phe Pro Pro Lys Tyr Gly Pro Pro Cys Pro Pro
                20                  25                  30

Cys Pro Ala Pro Glu Phe Leu Gly Gly Pro Ser Val Phe Leu Phe Pro
            35                  40                  45

Pro Lys
    50

<210> SEQ ID NO 17
<211> LENGTH: 52
<212> TYPE: PRT
<213> ORGANISM: Artificial
<220> FEATURE:
<223> OTHER INFORMATION: Disulfide-containing peptide

<400> SEQUENCE: 17

Tyr Gly Pro Pro Cys Pro Pro Cys Pro Ala Pro Glu Phe Leu Gly Gly
1               5                   10                  15

Pro Ser Val Phe Leu Phe Pro Pro Lys Tyr Gly Pro Pro Cys Pro Pro
                20                  25                  30

Cys Pro Ala Pro Glu Phe Leu Gly Gly Pro Ser Val Phe Leu Phe Pro
            35                  40                  45

Pro Lys Pro Lys
    50

<210> SEQ ID NO 18
<211> LENGTH: 35
<212> TYPE: PRT
<213> ORGANISM: Artificial
<220> FEATURE:
<223> OTHER INFORMATION: Disulfide-containing peptide

<400> SEQUENCE: 18

Thr Pro Glu Val Thr Cys Val Val Val Asp Val Ser Gln Glu Asp Pro
1               5                   10                  15

Glu Val Gln Phe Asn Trp Tyr Val Asp Gly Val Glu Val His Asn Ala
                20                  25                  30

Lys Cys Lys
    35

<210> SEQ ID NO 19
<211> LENGTH: 33
<212> TYPE: PRT
<213> ORGANISM: Artificial
<220> FEATURE:
<223> OTHER INFORMATION: Disulfide-containing peptide

<400> SEQUENCE: 19

Asn Gln Val Ser Leu Thr Cys Leu Val Lys Trp Gln Glu Gly Asn Val
1               5                   10                  15

Phe Ser Cys Ser Val Met His Glu Ala Leu His Asn His Tyr Thr Gln
                20                  25                  30

Lys
```

ANTIBODIES DIRECTED AGAINST T CELL IMMUNOGLOBULIN AND MUCIN PROTEIN 3 (TIM-3)

CROSS-REFERENCE TO RELATED APPLICATIONS

This application is a Continuation of U.S. patent application Ser. No. 16/346,463, filed on Apr. 30, 2019, which is a National Stage application under 35 U.S.C. § 371 of International Application No. PCT/US2017/059619, having an International Filing Date of Nov. 1, 2017, which claims the benefit of U.S. Provisional Application Ser. No. 62/416,131 filed Nov. 1, 2016, and 62/427,775 filed Nov. 29, 2016. The contents of the prior applications are hereby incorporated by reference in their entirety.

SEQUENCE LISTING

This document contains a Sequence Listing that has been submitted electronically as an ASCII text file named 26368-0063002_ST25.txt. The ASCII text file, created on Oct. 22, 2021, is 20 kilobytes in size. The material in the ASCII text file is hereby incorporated by reference in its entirety.

BACKGROUND

Cancer is a serious public health problem, with about 595,690 people in the United States of America expected to die of cancer in 2016 alone according to the American Cancer Society, Cancer Facts & FIGS. 2016.

BRIEF SUMMARY OF THE INVENTION

The protein T Cell Immunoglobulin and Mucin Domain-3 (TIM-3), also known as Hepatitis A Virus Cellular Receptor 2 (HAVCR2), is a Th1-specific cell surface protein that regulates macrophage activation and enhances the severity of experimental autoimmune encephalomyelitis in mice. TIM-3 is highly expressed on the surface of multiple immune cell types, including, for example, Th1 IFN-γ+ cells, Th17 cells, natural killer (NK) cells, monocytes, and tumor-associated dendritic cells (DCs) (see, e.g., Clayton et al., *J. Immunol.*, 192(2): 782-791 (2014); Jones et al., *J. Exp. Med.*, 205: 2763-2779 (2008); Monney et al., *Nature*, 415: 536-541 (2002); Hastings et al., *Eur. J. Immunol.*, 39: 2492-2501 (2009); Seki et al., *Clin. Immunol.*, 127: 78-88 (2008); Ju et al., *B. J. Hepatol.*, 52: 322-329 (2010); Anderson et al., *Science*, 318: 1141-1143 (2007); Baitsch et al., *PLoS ONE*, 7: e30852 (2012); Ndhlovu et al., *Blood*, 119: 3734-3743 (2012). TIM-3 also is highly expressed on "exhausted" or impaired CD8+ T-cells in a variety of chronic viral infections (e.g., HIV, HCV, and HBV) and in certain cancers (see, e.g., McMahan et al., *J. Clin. Invest.*, 120(12): 4546-4557 (2010); Jin et al., *Proc Natl Acad Sci USA*, 107(33): 14733-14738 (2010); Golden-Mason et al., *J. Virol.*, 83(18): 9122-9130 (2009); Jones et al., supra; Fourcade et al., *J. Exp. Med.*, 207(10): 2175-2186 (2010); Sakuishi et al., *J. Exp. Med.*, 207(10):2187-2194 (2010); Zhou et al., *Blood*, 117(17): 4501-4510 (2011); Ngiow et al., *Cancer Res.*, 71(10): 3540-3551 (2011)).

Putative ligands for TIM-3 include phosphatidylserine (Nakayama et al., *Blood*, 113: 3821-3830 (2009)), galectin-9 (Zhu et al., *Nat. Immunol.*, 6: 1245-1252 (2005)), high-mobility group protein 1 (HMGB1) (Chiba et al., *Nature Immunology*, 13: 832-842 (2012)), and carcinoembryonic antigen cell adhesion molecule 1 (CEACAM1) (Huang et al., *Nature*, 517(7534): 386-90 (2015)).

TIM-3 functions to regulate various aspects of the immune response. The interaction of TIM-3 and galectin-9 (Gal-9) induces cell death and in vivo blockade of this interaction exacerbates autoimmunity and abrogates tolerance in experimental models, strongly suggesting that TIM-3 is a negative regulatory molecule. In contrast to its effect on T-cells, the TIM-3-Gal-9 interaction exhibits antimicrobial effects by promoting macrophage clearance of intracellular pathogens (see, e.g., Sakuishi et al., *Trends in Immunology*, 32(8): 345-349 (2011)). In vivo, suppression of TIM-3 has been shown to enhance the pathological severity of experimental autoimmune encephalomyelitis (Monney et al., supra; and Anderson, A. C. and Anderson, D. E., *Curr. Opin. Immunol.*, 18: 665-669 (2006)). Studies also suggest that dysregulation of the TIM-3-galectin-9 pathway could play a role in chronic autoimmune diseases, such as multiple sclerosis (Anderson and Anderson, supra). TIM-3 promotes clearance of apoptotic cells by binding phosphatidyl serine through its unique binding cleft (see, e.g., DeKruyff et al., *J. Immunol.*, 184(4):1918-1930 (2010)).

Inhibition of TIM-3 activity, such as through use of monoclonal antibodies, is currently under investigation as an immunotherapy for tumors based on preclinical studies (see, e.g., Ngiow et al., *Cancer Res.*, 71(21): 1-5 (2011); Guo et al., *Journal of Translational Medicine*, 11: 215 (2013); and Ngiow et al., *Cancer Res.*, 71(21): 6567-6571 (2011)).

There is a need for additional antagonists of TIM-3 (e.g., an antibody) that binds TIM-3 with high affinity and effectively neutralizes TIM-3 activity.

The present disclosure provides antibody agents and various compositions and methods relating thereto including, for example, polypeptides, nucleic acids, cells, and various methodologies, etc.

The present invention provides novel antibodies that bind to TIM-3. In some embodiments, antibodies of the present invention bind to TIM-3 with high affinity and effectively neutralize TIM-3 activity. In some embodiments, antibody heavy chain polypeptide (SEQ ID NO:1) and light chain polypeptide (SEQ ID NO:2) sequences are explicitly provided.

The present disclosure provides a polypeptide or an isolated immunoglobulin heavy chain polypeptide having an amino acid sequence as set forth in SEQ ID NO:1. The present disclosure further provides a polypeptide or an isolated immunoglobulin heavy chain polypeptide having an amino acid sequence that shares at least about 90%, 91%, 92%, 93%, 94%, 95%, 96%, 97%, 98% or 99% overall identity with that set forth in SEQ ID NO:1. In some embodiments, sequence differences relative to the sequence set forth in SEQ ID NO:1 are not within the CDRs. In some embodiments, a polypeptide or an isolated immunoglobulin heavy chain polypeptide includes all three CDRs of SEQ ID NO:1. In some embodiments, a polypeptide or an immunoglobulin heavy chain polypeptide includes a signal peptide. In some embodiments, a polypeptide or an immunoglobulin heavy chain polypeptide which includes a signal peptide has an amino acid sequence as set forth in SEQ ID NO:5.

In some embodiments, a provided polypeptide or immunoglobulin heavy chain polypeptide is or comprises an IgG4 polypeptide. In some embodiments, a provided polypeptide or immunoglobulin heavy chain polypeptide comprises a human IGHG4*01 polypeptide. In some embodiments, a provided polypeptide or immunoglobulin heavy chain polypeptide comprises one or more mutations within the IgG heavy chain region. In some embodiments, a provided polypeptide or immunoglobulin heavy chain polypeptide comprises an IgG4 heavy chain constant region having one or more mutations in the heavy chain constant region. In some embodiments, a provided polypeptide or immunoglobulin heavy chain polypeptide comprises an IgG4 heavy chain constant region having one or more mutations in hinge region. It is envisioned that in some embodiments, a mutation in the IgG4 hinge region may prevent half molecule exchange with other IgG4 molecules. In some embodiments, the one or more mutations in hinge region of IgG4 may include a serine to proline stabilizing mutation that prevents half molecule exchange with other IgG4 molecules. In some embodiments, the one or more mutations in hinge region of IgG4 may include an S228P mutation. See, e.g., J. Biol. Chem. 2015; 290(9):5462-5469.

The present disclosure provides a polypeptide or an isolated immunoglobulin light chain polypeptide having an amino acid sequence as set forth in SEQ ID NO:2. The present disclosure further provides a polypeptide or an isolated immunoglobulin light chain polypeptide having an amino acid sequence that shares at least about 90%, 91%, 92%, 93%, 94%, 95%, 96%, 97%, 98% or 99% overall identity with that set forth in SEQ ID NO:2. In some embodiments, sequence differences relative to the sequence set forth in SEQ ID NO:2 are not within the CDRs. In some embodiments, a polypeptide or an isolated immunoglobulin light chain polypeptide includes all three CDRs of SEQ ID NO:2. In some embodiments, a provided polypeptide or immunoglobulin light chain polypeptide is a kappa light chain. In some embodiments, a provided polypeptide or immunoglobulin light chain polypeptide comprises a human IGKC*01 polypeptide. In some embodiments, a polypeptide or an immunoglobulin light chain polypeptide includes a signal peptide. In some embodiments, a polypeptide or an immunoglobulin light chain polypeptide includes a signal peptide has an amino acid sequence as set forth in SEQ ID NO:6.

In some embodiments, the present disclosure provides an anti-TIM-3 antibody agent comprising at least one immunoglobulin heavy chain having an amino acid sequence as set forth in SEQ ID NO:1 and at least one immunoglobulin light chain having an amino acid sequence as set forth in SEQ ID NO:2. In some embodiments an anti-TIM-3 antibody agent comprises two immunoglobulin heavy chains, each having an amino acid sequence as set forth in SEQ ID NO:1. Alternatively or additionally, in some embodiments an anti-TIM-3 antibody agent comprises two immunoglobulin light chains, each having an amino acid sequence as set forth in SEQ ID NO:2. In some embodiments, an anti-TIM-3 antibody agent has a canonical antibody format.

In some embodiments, a provided heavy chain, light chain and/or antibody agent is glycosylated and one or more sites. In some embodiments, a glycan is N-linked to an Fc region. In some embodiments, an antibody agent is glycosylated at Asn297 (Kabat numbering).

In some embodiments, present disclosure provides a composition comprising one or more glycoforms of a heavy chain, light chain, and/or antibody agent as described herein. In some embodiments, a provided composition comprises plurality of such glycoforms, present in specified absolute and/or relative amounts. In some embodiments, the present disclosure provides compositions that may be substantially free of one or more particular glycoforms of a heavy chain, light chain, and/or antibody agent as described herein.

In some embodiments, a provided heavy chain, light chain and/or antibody agent has a structure that includes one or more disulfide bonds. In some embodiments, the one or more disulfide bonds are or include a disulfide bond at the expected position for an IgG4 immunoglobulin.

In some embodiments, an anti-TIM-3 antibody agent is administered concurrently with another antibody agent, such as one specific for lymphocyte-activation gene 3 (LAG-3) or Programmed Death 1 (PD-1).

In some embodiments, an antibody agent binds to TIM-3 and another antigen, resulting in a "dual reactive" antibody agent (e.g., a bispecific antibody). For example, an antibody agent can bind to TIM-3 and to another negative regulator of the immune system such as, for example, programmed death 1 (PD-1) or Lymphocyte Activation Gene 3 protein (LAG-3).

In addition, the present disclosure provides isolated or purified nucleic acid sequences encoding the foregoing immunoglobulin polypeptides, vectors comprising such nucleic acid sequences, anti-TIM-3 antibody agents comprising the foregoing immunoglobulin polypeptides, nucleic acid sequences encoding such anti-TIM-3 antibody agents, vectors comprising such nucleic acid sequences, isolated cells comprising such vectors, compositions comprising such anti-TIM-3 antibody agents or such vectors with a pharmaceutically acceptable carrier, and methods of treating cancer, infectious diseases, or autoimmune diseases in mammals by administering effective amounts of such compositions to mammals.

BRIEF DESCRIPTION OF THE DRAWING

The Drawing included herein, which is composed of the following Figures, is for illustration purposes only and not for limitation.

(FIG. 2A) Target expression of PD-1 and TIM-3 in responsive (pre-stimulated) cells and exhausted (post-stimulated) cells. (FIG. 2B) Quantification of IFN-γ production in exhausted (post-stimulated) cells treated with an anti-TIM-3 antibody agent (black bars) and isotype control (clear bars).

DETAILED DESCRIPTION OF CERTAIN EMBODIMENTS

Figure 1:
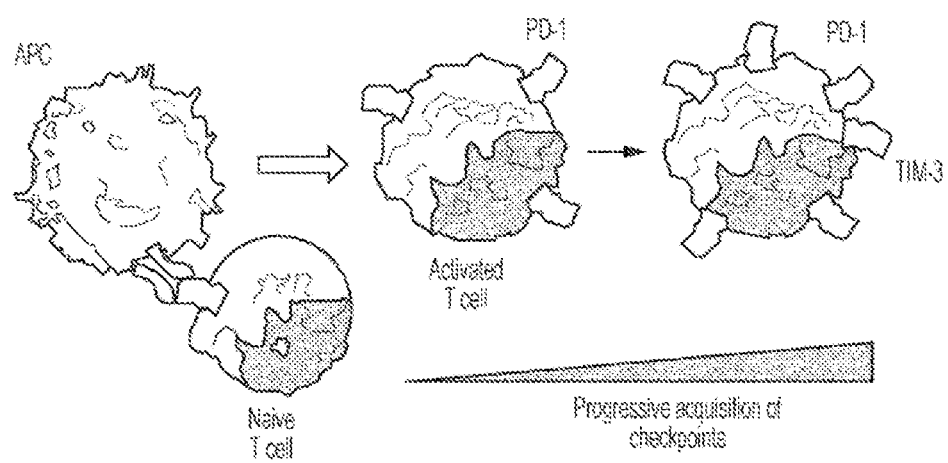
FIG. 1 depicts a schematic illustration, not to scale, of TIM-3 regulation of T cell activation.

The present disclosure provides antibody agents and various compositions and methods relating thereto including, for example, polypeptides, nucleic acids, cells, and various methodologies, etc. Antigen-binding proteins of the present invention bind to TIM-3 with high affinity and effectively neutralize TIM-3 activity. Immunoglobulin heavy chain polypeptide (SEQ ID NO:1 and 5) and immunoglobulin light chain polypeptide (SEQ ID NO:2 and 6) sequences are explicitly provided. In some embodiments, an immunoglobulin heavy chain polypeptide and/or an immunoglobulin light chain polypeptide is isolated. The term "immunoglobulin" or "antibody," as used herein, refers to a protein that is found in blood or other bodily fluids of vertebrates, which is used by the immune system to identify and neutralize foreign objects, such as bacteria and viruses. A whole immunoglobulin typically consists of four polypeptides: two identical copies of a heavy (H) chain polypeptide and two identical copies of a light (L) chain polypeptide. Each of the heavy chains contains one N-terminal variable ($V_H$) region and three C-terminal constant ($C_H1$, $C_H2$, and $C_H3$) regions, and each light chain contains one N-terminal variable ($V_L$) region and one C-terminal constant (C_L) region. Immunoglobulin light chains can be assigned to one of two distinct types, either kappa (κ) or lambda (λ), based upon the amino acid sequences of their constant domains. In a typical immunoglobulin, each light chain is linked to a heavy chain by disulphide bonds, and the two heavy chains are linked to each other by disulphide bonds. The light chain variable region is aligned with the variable region of the heavy chain, and the light chain constant region is aligned with the first constant region of the heavy chain. The remaining constant regions of the heavy chains are aligned with each other.

The variable regions of each pair of light and heavy chains form the antigen binding site of an antibody. $V_H$ and $V_L$ regions have the same general structure, with each region comprising four framework (FW or FR) regions, connected by three complementarity determining regions (CDRs). The term "framework region," as used herein, refers to the relatively conserved amino acid sequences within the variable region which are located between the hypervariable or complementary determining regions (CDRs). In a typical immunoglobulin, there are four framework regions in each variable domain, which are designated FR1, FR2, FR3, and FR4. The framework regions form β sheets that provide the structural framework of a variable region (see, e.g., C. A. Janeway et al. (eds.), *Immunobiology*, 5th Ed., Garland Publishing, New York, N.Y. (2001)).

In a typical immunoglobulin, there are three complementary determining regions (CDRs) in each variable domain, which are designated CDR1, CDR2, and CDR3. The CDRs form the "hypervariable region" of an antibody, which is responsible for antigen binding. The CDRs form loops connecting, and in some cases comprising part of, the β-sheet structure formed by the framework regions. While the constant regions of the light and heavy chains are not directly involved in binding of the antibody to an antigen, the constant regions can influence the orientation of the variable regions. The constant regions also exhibit various effector functions, such as participation in antibody-dependent complement-mediated lysis or antibody-dependent cellular toxicity via interactions with effector molecules and cells.

The disclosure provides, at least in part, antibody agents that bind to T Cell Immunoglobulin and Mucin Protein 3 (TIM-3). As used herein, the term "antibody agent" refers to an agent that specifically binds to a particular antigen. In some embodiments, the term encompasses any polypeptide or polypeptide complex that includes immunoglobulin structural elements sufficient to confer specific binding. Exemplary antibody agents include, but are not limited to monoclonal antibodies or polyclonal antibodies. In some embodiments, an antibody agent may include one or more constant region sequences that are characteristic of mouse, rabbit, primate, or human antibodies. In some embodiments, an antibody agent may include one or more sequence elements are humanized, primatized, chimeric, etc, as is known in the art. In many embodiments, the term "antibody agent" is used to refer to one or more of the art-known or developed constructs or formats for utilizing antibody structural and functional features in alternative presentation. For example, embodiments, an antibody agent utilized in accordance with the present invention is in a format selected from, but not limited to, intact IgA, IgG, IgE or IgM antibodies; bi- or multi-specific antibodies (e.g., Zybodies®, etc); antibody fragments such as Fab fragments, Fab' fragments, F(ab')₂ fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Trans-bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., poly-ethylene glycol, etc.]). In many embodiments, an antibody agent is or comprises a polypeptide whose amino acid sequence includes one or more structural elements recognized by those skilled in the art as a complementarity determining region (CDR); in some embodiments, an antibody agent is or comprises a polypeptide whose amino acid sequence includes at least one CDR (e.g., at least one heavy chain CDR and/or at least one light chain CDR) that is substantially identical to one found in a reference antibody. In some embodiments, an included CDR is substantially identical to a reference CDR in that it is either identical in sequence or contains between 1-5 amino acid substitutions as compared with the reference CDR. In some embodiments, an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments, an included CDR is substantially identical to a reference CDR in that it shows at least 96%, 96%, 97%, 98%, 99%, or 100% sequence identity with the reference CDR. In some embodiments, an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an included CDR is substantially identical to a reference CDR in that at least one amino acid within the included CDR is substituted as compared with the reference CDR but the included CDR has an amino acid sequence that is otherwise identical with that of the reference CDR. In some embodiments, an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

In some embodiments, an anti-TIM-3 antibody agent comprises an immunoglobulin heavy chain polypeptide and/or immunoglobulin light chain polypeptide. TIM-3 is a 60 kDa type 1 transmembrane protein comprised of three domains: an N-terminal Ig variable (IgV)-like domain, a central Ser/Thr-rich mucin domain, and a transmembrane domain with a short intracellular tail (see, e.g., Kane, L. P., *Journal of Immunology,* 184(6): 2743-2749 (2010)). TIM-3 was initially identified on terminally differentiated Th1 cells, and negatively regulates the T-cell response by inducing T-cell apoptosis (see, e.g., Hastings et al., *Eur. J. Immunol.,* 39(9): 2492-2501 (2009)). TIM-3 also is expressed on activated Th17 and Tc1 cells, and dysregulation of Tim-3 expression on CD4+ T-cells and CD8+ T-cells is associated with several autoimmune diseases, viral infections, and cancer (see, e.g., Liberal et al., *Hepatology,* 56(2): 677-686 (2012); Wu et al., *Eur. J Immunol.,* 42(5): 1180-1191 (2012); Anderson, A. C., *Curr. Opin. Immunol.,* 24(2): 213-216 (2012); and Han et al., *Frontiers in Immunology,* 4: 449 (2013)).

Certain other antibodies which bind to TIM-3, and components thereof, are known in the art (see, e.g., U.S. Pat. Nos. 8,101,176; 8,552,156; and 8,841,418). Certain anti-TIM-3 antibodies also are commercially available from sources such as, for example, Abcam (Cambridge, Mass.), and R&D Systems, Inc. (Minneapolis, Minn.).

In some embodiments, a provided heavy chain, light chain and/or antibody agent is glycosylated and one or more sites. As used herein, "glycan" is a sugar polymer (moiety) component of a glycoprotein. The term "glycan" encompasses free glycans, including glycans that have been cleaved or otherwise released from a glycoprotein. In some embodiments, a glycan is N-linked to an Fc region. In some embodiments, an antibody agent is glycosylated at Asn297 (Kabat numbering).

In some embodiments, present disclosure provides a composition comprising one or more glycoforms of a heavy chain, light chain, and/or antibody agent as described herein. The term "glycoform" is used herein to refer to a particular form of a glycoprotein. That is, when a glycoprotein includes a particular polypeptide that has the potential to be linked to different glycans or sets of glycans, then each different version of the glycoprotein (i.e., where the polypeptide is linked to a particular glycan or set of glycans) is referred to as a "glycoform." In some embodiments, a provided composition comprises a plurality of glycoforms of one or more of a heavy chain, light chain, and/or antibody agent as described herein. In some embodiments, a provided composition comprises plurality of such glycoforms, present in specified absolute and/or relative amounts. In some embodiments, the present disclosure provides compositions that may be substantially free of one or more particular glycoforms of a heavy chain, light chain, and/or antibody agent as described herein.

In some embodiments, an amount of a glycoform is expressed as a "percent." For any given parameter, "percent" refers to the number of moles of a particular glycan (glycan X) relative to total moles of glycans of a preparation. In some embodiments, "percent" refers to the number of moles of PNGase F-released Fc glycan X relative to total moles of PNGase F-released Fc glycans detected.

In some embodiments, a provided heavy chain, light chain and/or antibody agent has a structure that includes one or more disulfide bonds. In some embodiments, the one or more disulfide bonds are or include a disulfide bond at the expected position for an IgG4 immunglobulin. In some embodiments, a disulfide bond is present at one or more residues corresponding to positions selected from residue 22, 96, 127, 140, 196, 219, 222, 254, 314, 360 and 418 of SEQ ID NO: 1. In some embodiments, a disulfide bond is present at one or more residues corresponding to positions selected from residue 23, 88, 134, 194 and 214 of SEQ ID NO: 2. In some embodiments, a provided TIM-3 antibody agent comprises one or more disulfide bonds, wherein the first cysteine is selected from residue 22, 96, 127, 140, 196, 219, 222, 254, 314, 360 and 418 of SEQ ID NO: 1, and the second cysteine is selected from residue 23, 88, 134, 194, and 214 of SEQ ID NO: 2. In some embodiments, a provided TIM-3 antibody agent comprises one or more disulfide bonds, wherein the first cysteine is selected from residue 22, 96, 127, 140, 196, 219, 222, 254, 314, 360 and 418 of SEQ ID NO: 1, and the second cysteine is selected from 22, 96, 127, 140, 196, 219, 222, 254, 314, 360 and 418 of SEQ ID NO: 1. In some embodiments, a provided TIM-3 antibody agent comprises one or more disulfide bonds, wherein the first cysteine is selected from residue 23, 88, 134, 194, and 214 of SEQ ID NO: 2, and the second cysteine is selected from residue 23, 88, 134, 194, and 214 of SEQ ID NO: 2.

In some embodiments, a provided TIM-3 antibody agent comprises one or more disulfide bonds formed by a first cysteine and a second cysteine, wherein the one or more disulfide bond is selected from: (a) the first residue is residue 23 of SEQ ID NO: 2, and the second residue is residue 88 of SEQ ID NO: 2; (b) the first residue is residue 134 of SEQ ID NO: 2, and the second residue is residue 194 of SEQ ID NO: 2; (c) the first residue is residue 214 of SEQ ID NO: 2, and the second residue is residue 127 of SEQ ID NO: 1; (d) the first residue is residue 22 of SEQ ID NO: 1, and the second residue is residue 97 of SEQ ID NO: 1; (e) the first residue is residue 140 of SEQ ID NO: 1, and the second residue is residue 196 of SEQ ID NO: 1; (f) the first residue is residue 219 of SEQ ID NO: 1, and the second residue is residue 222 of SEQ ID NO: 1; (g) the first residue is residue 254 of SEQ ID NO: 1, and the second residue is residue 314 of SEQ ID NO: 1; and (h) the first residue is residue 360 of SEQ ID NO: 1, and the second residue is residue 418 of SEQ ID NO: 1. In some embodiments, a provided TIM-3 antibody agent comprises disulfide bonds formed by a first cysteine and a second cysteine, wherein the antibody agent includes disulfide bonds at each of: (a) the first residue is residue 23 of SEQ ID NO: 2, and the second residue is residue 88 of SEQ ID NO: 2; (b) the first residue is residue 134 of SEQ ID NO: 2, and the second residue is residue 194 of SEQ ID NO: 2; (c) the first residue is residue 214 of SEQ ID NO: 2, and the second residue is residue 127 of SEQ ID NO: 1; (d) the first residue is residue 22 of SEQ ID NO: 1, and the second residue is residue 97 of SEQ ID NO: 1; (e) the first residue is residue 140 of SEQ ID NO: 1, and the second residue is residue 196 of SEQ ID NO: 1; (f) the first residue is residue 219 of SEQ ID NO: 1, and the second residue is residue 222 of SEQ ID NO: 1; (g) the first residue is residue 254 of SEQ ID NO: 1, and the second residue is residue 314 of SEQ ID NO: 1; and (h) the first residue is residue 360 of SEQ ID NO: 1, and the second residue is residue 418 of SEQ ID NO: 1.

In some embodiments, an isolated immunoglobulin heavy chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 1 or 5.

In some embodiments, an isolated immunoglobulin light chain polypeptide which comprises an amino acid sequence that is at least 90% identical (e.g., at least 91%, at least 92%, at least 93%, at least 94%, at least 95%, at least 96%, at least 97%, at least 98%, at least 99%, or 100% identical) to SEQ ID NO: 2 or 6.

Nucleic acid or amino acid sequence "identity," as described herein, can be determined by comparing a nucleic acid or amino acid sequence of interest to a reference nucleic acid or amino acid sequence. The percent identity is the number of nucleotides or amino acid residues that are the same (i.e., that are identical) as between the sequence of interest and the reference sequence divided by the length of the longest sequence (i.e., the length of either the sequence of interest or the reference sequence, whichever is longer). A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FAS™, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA,* 106(10): 3770-3775 (2009), Durbin et al., eds., *Biological Sequence Analysis: Probalistic Models of Proteins and Nucleic Acids*, Cambridge University Press, Cambridge, UK (2009), Soding, *Bioinformatics,* 21(7): 951-960 (2005), Altschul et al., *Nucleic Acids Res.,* 25(17): 3389-3402 (1997), and Gusfield, *Algorithms on Strings, Trees and Sequences*, Cambridge University Press, Cambridge UK (1997)).

One or more amino acids of the aforementioned immunoglobulin heavy chain polypeptides and/or light chain polypeptides can be replaced or substituted with a different amino acid. An amino acid "replacement" or "substitution" refers to the replacement of one amino acid at a given position or residue by another amino acid at the same position or residue within a polypeptide sequence.

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or He), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gin), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

An amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, Principles of Protein Structure, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —NH$_2$ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

The present disclosure provides, at least in part, an isolated anti-TIM-3 antibody agent comprising, consisting essentially of, or consisting of an inventive isolated amino acid sequences described herein. As used herein, the term "isolated" (or "purified") refers to a nucleic acid sequence (e.g., a polynucleotide) or an amino acid sequence (e.g., a polypeptide) that is removed or separated from other components present in its natural environment. For example, an isolated polypeptide is one that is separated from other components of a cell in which it was produced (e.g., the endoplasmic reticulum or cytoplasmic proteins and RNA). An isolated polynucleotide is one that is separated from other nuclear components (e.g., histones) and/or from upstream or downstream nucleic acid sequences. An isolated nucleic acid sequence or amino acid sequence can be at least 60% free, or at least 75% free, or at least 90% free, or at least 95% free, or at least 98% free, or at least 99% free from other components present in natural environment of the indicated nucleic acid sequence or amino acid sequence.

By "anti-TIM-3 antibody agent" is meant a molecule, preferably a proteinaceous molecule, that binds specifically to a TIM-3 protein. In some embodiments, a TIM-3 binding agent is an anti-TIM-3 antibody agent. In some embodiments, an isolated anti-TIM-3 antibody agent comprises, consists essentially of, or consists of an immunoglobulin heavy chain polypeptide (e.g., SEQ ID NO:1) and/or an immunoglobulin light chain polypeptide (e.g., SEQ ID NO:2). In some embodiments, an isolated anti-TIM-3 antibody agent comprises, consists essentially of, or consists of an immunoglobulin heavy chain polypeptide whose sequence comprises SEQ ID NO:1 and an immunoglobulin light chain polypeptide whose sequence comprises SEQ ID NO:2.

In some embodiments, a provided polypeptide or heavy chain polypeptide consists essentially of an amino acid sequence of SEQ ID NO: 1 or SEQ ID NO: 5, and may further comprise additional components that do not materially affect the polypeptide, e.g., by influencing affinity of an inventive heavy chain polypeptide to TIM-3. Examples of such components include, for example, protein moieties such as biotin that facilitate purification or isolation, passenger mutations, sequences free of problematic sites including free cysteines, additional glycosylation sites, and high-likelihood deamidation or isomerization sites.

In some embodiments, a provided polypeptide or immunoglobulin heavy chain polypeptide consists of an amino acid sequence of SEQ ID NO: 1 or SEQ ID NO: 5 and does not comprise any additional components (i.e., components that are not endogenous to an inventive immunoglobulin heavy chain polypeptide).

In some embodiments, anti-TIM-3 antibody agents include variants where one or more amino acids in the immunoglobulin heavy chain polypeptide and/or the immunoglobulin light chain polypeptide replaced, in any combination, with a different amino acid residue, or can be deleted or inserted, so long as the biological activity of an anti-TIM-3 antibody agent is not materially diminished (e.g., enhanced or improved) as a result of the amino acid replacements, insertions, and/or deletions. The "biological activity" of an TIM-3-binding agent refers to, for example, binding affinity for a particular TIM-3 epitope, neutralization or inhibition of TIM-3 binding to its receptor(s), neutralization or inhibition of TIM-3 activity in vivo (e.g., $IC_{50}$), pharmacokinetics, and cross-reactivity (e.g., with non-human homologs or orthologs of the TIM-3 protein, or with other proteins or tissues). Other biological properties or characteristics of an antigen-binding agent recognized in the art include, for example, avidity, selectivity, solubility, folding, immunotoxicity, expression, and formulation. The aforementioned properties or characteristics can be observed, measured, and/or assessed using standard techniques including, but not limited to, ELISA, competitive ELISA, surface plasmon resonance analysis (BIACORE™), or Kinetic Exclusion Assay (KINEXA™), in vitro or in vivo neutralization assays, receptor-ligand binding assays, cytokine or growth factor production and/or secretion assays, and signal transduction and immunohistochemistry assays.

The terms "inhibit" or "neutralize," as used herein with respect to the activity of an anti-TIM-3 antibody agent, refer to the ability to substantially antagonize, prohibit, prevent, restrain, slow, disrupt, alter, eliminate, stop, or reverse the progression or severity of, for example, the biological activity of TIM-3, or a disease or condition associated with TIM-3. In some embodiments, an anti-TIM-3 antibody agent inhibits or neutralizes the activity of TIM-3 by at least about 20%, about 30%, about 40%, about 50%, about 60%, about 70%, about 80%, about 90%, about 95%, about 98%, about 99%, about 100%, or a range defined by any two of the foregoing values (e.g., 20% to 100%, 40% to 100% or 60% to 95%, etc.)

In some embodiments, an anti-TIM-3 antibody agent is a whole antibody or a fragment thereof (e.g., an antibody fragment). In some embodiments, the antibody or antibody fragment comprises a heavy chain constant region that is based upon wild-type IgG1, IgG2, or IgG4 antibodies, or variants thereof. It will be appreciated that each antibody class, or isotype, engages a distinct set of effector mechanisms for disposing of or neutralizing antigen once recognized. As such, in some embodiments, when an anti-TIM-3 antibody agent is an antibody, it can exhibit one or more effector functions, such as participation in antibody-dependent complement-mediated lysis or antibody-dependent cellular toxicity via interactions with effector molecules and cells (e.g., activation of the complement system).

In some embodiments, an anti-TIM-3 antibody agent comprises an IgG4 heavy chain constant region. In some embodiments, an anti-TIM-3 antibody agent comprises one or more mutations within the IgG heavy chain region. In some embodiments, an anti-TIM-3 antibody agent comprises an IgG4 heavy chain constant region having one or more mutations in the heavy chain constant region. In some embodiments, an anti-TIM-3 antibody agent comprises an IgG4 heavy chain constant region having one or more mutations in hinge region. It is envisioned that in some embodiments, a mutation in the IgG4 hinge region may prevent half molecule exchange with other IgG4 molecules. In some embodiments, the one or more mutations in hinge region of IgG4 may include an S228P mutation or a serine to proline stabilizing mutation that prevents half molecule exchange with other IgG4 molecules. See, e.g., J. Biol. Chem. 2015; 290(9):5462-5469.

An anti-TIM-3 antibody agent also can be an antibody conjugate. In this respect, an anti-TIM-3 antibody agent can be a conjugate of (1) an anti-TIM-3 antibody and (2) a protein or non-protein moiety. For example, an anti-TIM-3 antibody agent can be an antibody conjugated to a peptide, a fluorescent molecule, or a chemotherapeutic agent.

An anti-TIM-3 antibody agent can be, or can be obtained from, a human antibody, a non-human antibody, or a chimeric antibody. By "chimeric" is meant an antibody or fragment thereof comprising both human and non-human regions. In some embodiments, an anti-TIM-3 antibody agent is a humanized antibody. A "humanized" antibody is a monoclonal antibody comprising a human antibody scaffold and at least one CDR obtained or derived from a non-human antibody. Non-human antibodies include antibodies isolated from any non-human animal, such as, for example, a rodent (e.g., a mouse or rat). A humanized antibody can comprise, one, two, or three CDRs obtained or derived from a non-human antibody. In some embodiments, CDRH3 of an inventive TIM-3-binding agent is obtained or derived from a mouse monoclonal antibody, while the remaining variable regions and constant region of an anti-TIM-3 antibody agent are obtained or derived from a human monoclonal antibody.

A human antibody, a non-human antibody, a chimeric antibody, or a humanized antibody can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and Janeway et al. (eds.), *Immunobiology, 5th Ed.*, Garland Publishing, New York, N.Y. (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™, and the Kyowa Kirin KM-MOUSE™ (see, e.g., Lonberg, *Nat. Biotechnol.*, 23(9): 1117-25 (2005), and Lonberg, *Handb. Exp. Pharmacol.*, 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, N.J. (2009)), including, e.g., grafting of non-human CDRs onto a human antibody scaffold (see, e.g., Kashmiri et al., *Methods*, 36(1): 25-34 (2005); and Hou et al., *J. Biochem.*, 144(1): 115-120 (2008)). In some embodiments, a humanized antibody can be produced using the methods described in, e.g., U.S. Patent Application Publication 2011/0287485 A1.

In some embodiments, an anti-TIM-3 antibody agent binds an epitope of TIM-3 which blocks the binding of TIM-3 to any of its putative ligands (e.g., phosphatidylserine, galectin-9, high-mobility group protein 1 (HMGB1), and carcinoembryonic antigen cell adhesion molecule 1 (CEACAM1)) and inhibits TIM-3-mediated signaling. The disclosure also provides an isolated or purified epitope of TIM-3 which blocks the binding of TIM-3 to any of its putative ligands in an indirect or allosteric manner. In some embodiments, an anti-TIM-3 antibody agent binds an epitope of TIM-3 which blocks the binding of TIM-3 to one, two or more of its putative ligands.

The disclosure also provides one or more isolated or purified nucleic acid sequences that encode an inventive immunoglobulin heavy chain polypeptide, an inventive immunoglobulin light chain polypeptide, and/or an inventive anti-TIM-3 antibody agent.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like). Nucleic acid sequences encoding an inventive immunoglobulin heavy chain polypeptides include, for example, SEQ ID NO: 3. Nucleic acid sequences encoding an inventive immunoglobulin light chain polypeptides include, for example, SEQ ID NO: 4.

The disclosure further provides a vector comprising one or more nucleic acid sequences encoding an inventive immunoglobulin heavy chain polypeptide, an inventive immunoglobulin light chain polypeptide, and/or an inventive anti-TIM-3 antibody agent. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual*, 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

In addition to the nucleic acid sequence encoding an inventive polypeptide, an inventive immunoglobulin heavy polypeptide, an inventive immunoglobulin light chain polypeptide, and/or an inventive anti-TIM-3 antibody agent, the vector can comprise expression control sequences, such as promoters, enhancers, polyadenylation signals, transcription terminators, signal peptides (e.g., the osteonectin signal peptide), internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, Calif.), LACSWITCH™ system (Stratagene, San Diego, Calif.), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked.

Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA*, 77: 3567-3570 (1980); O'Hare et al., *Proc. Natl. Acad. Sci. USA*, 78: 1527-1531 (1981); Mulligan & Berg, *Proc. Natl. Acad. Sci. USA*, 78: 2072-2076 (1981); Colberre-Garapin et al., *J. Mol. Biol.*, 150: 1-14 (1981); Santerre et al., *Gene*, 30: 147-156 (1984); Kent et al., *Science*, 237: 901-903 (1987); Wigler et al., *Cell*, 11: 223-232 (1977); Szybalska & Szybalski, *Proc. Natl. Acad. Sci. USA*, 48: 2026-2034 (1962); Lowy et al., *Cell*, 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy*, 11: 1735-

1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNA™5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Life Technologies (Carlsbad, Calif.), UCOE from Millipore (Billerica, Mass.), and pCI or pFN10A (ACT) FLEXI™ from Promega (Madison, Wis.).

Viral vectors also can be used. Representative commercially available viral expression vectors include, but are not limited to, the adenovirus-based Per.C6 system available from Crucell, Inc. (Leiden, The Netherlands), the lentiviral-based pLP1 from Invitrogen (Carlsbad, Calif.), and the retroviral vectors pFB-ERV plus pCFB-EGSH from Stratagene (La Jolla, Calif.).

Nucleic acid sequences encoding inventive amino acid sequences can be provided to a cell on the same vector (i.e., in cis). A unidirectional promoter can be used to control expression of each nucleic acid sequence. In some embodiments, a combination of bidirectional and unidirectional promoters can be used to control expression of multiple nucleic acid sequences. Nucleic acid sequences encoding inventive amino acid sequences alternatively can be provided to the population of cells on separate vectors (i.e., in trans). Each of the nucleic acid sequences in each of the separate vectors can comprise the same or different expression control sequences. The separate vectors can be provided to cells simultaneously or sequentially.

The vector(s) comprising the nucleic acid(s) encoding inventive amino acid sequences can be introduced into a host cell that is capable of expressing the polypeptides encoded thereby, including any suitable prokaryotic or eukaryotic cell. As such, the present disclosure provides an isolated cell comprising an inventive vector. Host cells include cells that can be easily and reliably grown, have reasonably fast growth rates, have well-characterized expression systems, and can be transformed or transfected easily and efficiently.

Examples of suitable prokaryotic cells include, but are not limited to, cells from the genera Bacillus (such as Bacillus subtilis and Bacillus brevis), Escherichia (such as E. coli), Pseudomonas, Streptomyces, Salmonella, and Erwinia. Useful prokaryotic cells include, for example, the various strains of Escherichia coli (e.g., K12, HB101 (ATCC No. 33694), DH5α, DH10, MC1061 (ATCC No. 53338), and CC102).

In some embodiments, an inventive vector is introduced into a eukaryotic cell. Suitable eukaryotic cells are known in the art and include, for example, yeast cells, insect cells, and mammalian cells. Examples of suitable yeast cells include those from the genera Kluyveromyces, Pichia, Rhino-sporidium, Saccharomyces, and Schizosaccharomyces. Yeast cells include, for example, Saccharomyces cerivisae and Pichia pastoris.

Suitable insect cells are described in, for example, Kitts et al., Biotechniques, 14: 810-817 (1993); Lucklow, Curr. Opin. Biotechnol., 4: 564-572 (1993); and Lucklow et al., J. Virol., 67: 4566-4579 (1993). Insect cells include, for example, Sf-9 and HI5 (Invitrogen, Carlsbad, Calif.).

In some embodiments, mammalian cells are utilized. A number of suitable mammalian host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al., Proc. Natl. Acad. Sci. USA, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

In some embodiments, the mammalian cell is a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), DT40 (CRL-2111), 18-81 (Jack et al., Proc. Natl. Acad. Sci. USA, 85: 1581-1585 (1988)), Raji cells (CCL-86), PER.C6 cells (Crucell Holland B. V., Leiden, The Netherlands), and derivatives thereof.

A nucleic acid sequence encoding an inventive amino acid sequence may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)). Phage or viral vectors can be introduced into host cells, after growth of infectious particles in suitable packaging cells, many of which are commercially available.

The disclosure provides a composition comprising an effective amount of an inventive immunoglobulin heavy chain polypeptide, an inventive immunoglobulin light chain polypeptide, an inventive TIM-3-binding agent, an inventive nucleic acid sequence encoding any of the foregoing, or an inventive vector comprising an inventive nucleic acid sequence. In some embodiments, the composition is a pharmaceutically acceptable (e.g., physiologically acceptable) composition, which comprises a carrier, preferably a pharmaceutically acceptable (e.g., physiologically acceptable) carrier, and inventive amino acid sequences, antigen-binding agent, or vector. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: *The Science and Practice of Pharmacy*, 21st Edition, Lippincott Williams & Wilkins, Philadelphia, Pa. (2001).

The disclosure further provides methods of treating any disease or disorder in which expression, improper expression (e.g., overexpression) or increased activity of a TIM-3 protein causes or contributes to the pathological effects of the disease, or a decrease in TIM-3 protein levels or activity has a therapeutic benefit in mammals, such as humans. Mammals include, e.g., mice, rats, rabbits, dogs, cats, cows, horses, non-human primates, and humans.

TIM-3 is a negative regulator of the immune response and is therefore a target for therapy (FIG. 1). Accordingly, the disclosure further provides methods of treating a disorder in a mammal that is responsive to TIM-3 inhibition or neutralization. The method comprises administering the aforementioned composition to a mammal having a disorder that is responsive to TIM-3 inhibition or neutralization, whereupon the disorder is treated in the mammal. A disorder that is "responsive to TIM-3 inhibition" or "responsive to TIM-3 neutralization" refers to any disease or disorder in which a decrease in TIM-3 levels or activity has a therapeutic benefit in mammals, for example humans, or the improper expression (e.g., overexpression) or increased activity of TIM-3 causes or contributes to the pathological effects of the disease or disorder. Disorders that are responsive to TIM-3 inhibition include, for example, cancer, infectious diseases, and autoimmune diseases.

The disclosure further provides methods of enhancing an immune response or increasing the activity of an immune cell in a mammal having a disorder that is responsive to TIM-3 inhibition. In some embodiments, such methods include administering an effective amount of any TIM-3 binding agent or antibody agent described herein. In some embodiments, administration of a TIM-3 binding agent enhances or increases an immune response or immune cell activity in a mammal or tissue thereof. In some embodiments, an immune response is a humoral or cell mediated immune response. In some embodiments, an immune response is a CD4 or CD8 T cell response. In some embodiments, an immune response is a B cell response.

The inventive methods can be used to treat any type of cancer known in the art, such as, for example, melanoma, renal cell carcinoma, lung cancer, bladder cancer, breast cancer, cervical cancer, colon cancer, gall bladder cancer, laryngeal cancer, liver cancer, thyroid cancer, stomach cancer, salivary gland cancer, prostate cancer, pancreatic cancer, adenocarcinoma (e.g., adenocarcinoma of the lung), or Merkel cell carcinoma (see, e.g., Bhatia et al., *Curr. Oncol. Rep.*, 13(6): 488-497 (2011)). In some embodiments, a cancer is endometrial cancer, breast cancer, ovarian cancer, cervical cancer, fallopian tube cancer, testicular cancer, primary peritoneal cancer, colon cancer, colorectal cancer, stomach cancer, small intestine cancer, squamous cell carcinoma of the anogenital region, melanoma, renal cell carcinoma, lung cancer, non-small cell lung cancer, squamous cell carcinoma of the lung, stomach cancer, bladder cancer, gall bladder cancer, liver cancer, thyroid cancer, laryngeal cancer, salivary gland cancer, esophageal cancer, head and neck cancer, squamous cell carcinoma of the head and neck, adenocarcinoma, adenocarcinoma of the lung, prostate cancer, pancreatic cancer, mesothelioma, Merkel cell carcinoma, sarcoma, glioblastoma, or hematological cancer (e.g., multiple myeloma, B-cell lymphoma, T-cell lymphoma, Hodgkin's lymphoma/primary mediastinal B-cell lymphoma, or chronic myelogenous leukemia). In some embodiments, a cancer to be treated with the inventive methods and/or compositions described herein is characterized by microsatellite instability or lack thereof. Microsatellite instability ("MSI") is or comprises a change that in the DNA of certain cells (such as tumor cells) in which the number of repeats of microsatellites (short, repeated sequences of DNA) is different than the number of repeats that was contained in the DNA from which it was inherited. Microsatellite instability arises from a failure to repair replication-associated errors due to a defective DNA mismatch repair (MMR) system. This failure allows persistence of mismatch mutations all over the genome, but especially in regions of repetitive DNA known as microsatellites, leading to increased mutational load. It has been demonstrated that at least some tumors characterized by MSI-H have improved responses to certain anti-PD-1 agents (Le et al., (2015) *N. Engl. J. Med.* 372(26):2509-2520; Westdorp et al., (2016) *Cancer Immunol. Immunother.* 65(10):1249-1259).

In some embodiments, a cancer has a microsatellite instability status of high microsatellite instability (e.g., MSI-H status). In some embodiments, a cancer has a microsatellite instability status of low microsatellite instability (e.g., MSI-L status). In some embodiments, a cancer has a microsatellite instability status of microsatellite stable (e.g., MSS status). In some embodiments microsatellite instability status is assessed by a next generation sequencing (NGS)-based assay, an immunohistochemistry (IHC)-based assay, and/or a PCR-based assay. In some embodiments, microsatellite instability is detected by NGS. In some embodiments, microsatellite instability is detected by IHC. In some embodiments, microsatellite instability is detected by PCR.

In embodiments, the cancer is associated with a high tumor mutation burden (TMB). In some embodiments, the cancer is associated with high TMB and MSI-H. In some embodiments, the cancer is associated with high TMB and MSI-L or MSS. In some embodiments, the cancer is endometrial cancer associated with high TMB. In some related embodiments, the endometrial cancer is associated with high TMB and MSI-H. In some related embodiments, the endometrial cancer is associated with high TMB and MSI-L or MSS.

In some embodiments, a cancer is a mismatch repair deficient cancer. Microsatellite instability may arise from a failure to repair replication-associated errors due to a defective DNA mismatch repair (MMR) system. This failure allows persistence of mismatch mutations all over the genome, but especially in regions of repetitive DNA known as microsatellites, leading to increased mutational load that may improve responses to certain anti-PD-1 agents. Id. In some embodiments, a cancer is a hypermutated cancer. In some embodiments, a cancer harbors a mutation in polymerase epsilon (POLE).

The inventive methods can be used to treat any type of infectious disease (i.e., a disease or disorder caused by a bacterium, a virus, a fungus, or a parasite). Examples of infectious diseases that can be treated by the inventive method include, but are not limited to, diseases caused by a human immunodeficiency virus (HIV), a respiratory syncytial virus (RSV), an influenza virus, a dengue virus, a hepatitis B virus (HBV, or a hepatitis C virus (HCV)).

The inventive methods can be used to treat any type of autoimmune disease (i.e., as disease or disorder caused by immune system over-activity in which the body attacks and damages its own tissues), such as those described in, for example, MacKay I. R. and Rose N. R., eds., *The Autoimmune Diseases, Fifth Edition*, Academic Press, Waltham, Mass. (2014). Examples of autoimmune diseases that can be treated by the inventive method include, but are not limited to, multiple sclerosis, type 1 diabetes mellitus, rheumatoid arthritis, scleroderma, Crohn's disease, psoriasis, systemic lupus erythematosus (SLE), and ulcerative colitis.

Administration of a composition comprising an inventive immunoglobulin heavy chain polypeptide, an inventive immunoglobulin light chain polypeptide, an inventive TIM-3-binding agent, an inventive nucleic acid sequence encoding any of the foregoing, or an inventive vector comprising an inventive nucleic acid sequence induces an immune response against a cancer or infectious disease in a mammal. Mammals include, e.g., mice, rats, rabbits, dogs, cats, cows, horses, non-human primates, and humans. An "immune response" can entail, for example, antibody production and/or the activation of immune effector cells (e.g., T-cells).

As used herein, the terms "treatment," "treating," and the like refer to obtaining a desired pharmacologic and/or physiologic effect. In some embodiments, the effect is therapeutic, i.e., the effect partially or completely cures a disease and/or adverse symptom attributable to the disease. To this end, the inventive method comprises administering a "therapeutically effective amount" of an anti-TIM-3 antibody agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of an anti-TIM-3 antibody agent to elicit a desired response in the individual. For example, a therapeutically effective amount of an anti-TIM-3 antibody agent is an amount which decreases TIM-3 bioactivity in a human.

Additionally or alternatively, the pharmacologic and/or physiologic effect may be prophylactic, i.e., the effect completely or partially prevents a disease or symptom thereof. In this respect, the inventive method comprises administering a "prophylactically effective amount" of an anti-TIM-3 antibody agent. A "prophylactically effective amount" refers to an amount effective, at dosages and for periods of time necessary, to achieve a desired prophylactic result (e.g., prevention of disease onset).

A typical dose can be, for example, in the range of 1 pg/kg to 20 mg/kg of animal or human body weight; however, doses below or above this exemplary range are within the scope of the invention. The daily parenteral dose can be about 0.00001 µg/kg to about 20 mg/kg of total body weight (e.g., about 0.001 µg/kg, about 0.1 µg/kg, about 1 µg/kg, about 5 µg/kg, about 10 µg/kg, about 100 µg/kg, about 500 µg/kg, about 1 mg/kg, about 5 mg/kg, about 10 mg/kg, or a range defined by any two of the foregoing values). In some embodiments, from about 0.1 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values). In some embodiments, from about 1 µg/kg to 5 mg/kg of total body weight (e.g., about 3 µg/kg, about 15 µg/kg, about 75 µg/kg, about 300 µg/kg, about 900 µg/kg, about 2 mg/kg, about 4 mg/kg, or a range defined by any two of the foregoing values). In some embodiments, from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs, or alternatively, the treatment can be continued for the lifetime of the patient. However, other dosage regimens may be useful and are within the scope of the invention. The desired dosage can be delivered by a single bolus administration of the composition, by multiple bolus administrations of the composition, or by continuous infusion administration of the composition.

Composition(s) comprising an effective amount of an inventive immunoglobulin heavy chain polypeptide, an inventive immunoglobulin light chain polypeptide, an inventive TIM-3-binding agent, an inventive nucleic acid sequence encoding any of the foregoing, or an inventive vector comprising an inventive nucleic acid sequence can be administered to a mammal using standard administration techniques, including oral, ocular, parenteral, intravenous, intraperitoneal, subcutaneous, pulmonary, bronchial, buccal, intradermal, interdermal, transdermal, topical, intramuscular, intranasal, buccal, sublingual, enteral, intra-arterial, intragastric, within a specific organ (e.g., intrahepatic), rectally, subcutaneously, sublingual, tracheal, vaginal, vitreal, intramedullar, intrathecal, intraventricular, mucosal or suppository administration. In some embodiments, the composition is suitable for parenteral administration. The term "parenteral," as used herein, includes intravenous, intramuscular, subcutaneous, rectal, vaginal, and intraperitoneal administration. In some embodiments, the composition is administered to a mammal using peripheral systemic delivery by intravenous, intraperitoneal, or subcutaneous injection. Mammals include, e.g., mice, rats, rabbits, dogs, cats, cows, horses, non-human primates, and humans.

Once administered to a mammal (e.g., a human), the biological activity of an anti-TIM-3 antibody agent can be measured by any suitable method known in the art. For example, the biological activity can be assessed by determining the stability of a particular TIM-3-binding agent. In some embodiments, an anti-TIM-3 antibody agent (e.g., an antibody) has an in vivo half-life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values). In some embodiments, an anti-TIM-3 antibody agent has an in vivo half life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In some embodiments, an anti-TIM-3 antibody agent has an in vivo half-life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values).

The stability of an anti-TIM-3 antibody agent can be measured using any other suitable assay known in the art, such as, for example, measuring serum half-life, differential scanning calorimetry (DSC), thermal shift assays, and pulse-chase assays. Other methods of measuring protein stability in vivo and in vitro that can be used in the context of the invention are described in, for example, *Protein Stability and Folding*, B. A. Shirley (ed.), Human Press, Totowa, N.J. (1995); *Protein Structure, Stability, and Interactions (Methods in Molecular Biology)*, Shiver J. W. (ed.), Humana Press, New York, N.Y. (2010); and Ignatova, *Microb. Cell Fact.*, 4: 23 (2005).

The stability of an anti-TIM-3 antibody agent can be measured in terms of the transition mid-point value ($T_m$), which is the temperature where 50% of the amino acid sequence is in its native confirmation, and the other 50% is denatured. In general, the higher the $T_m$, the more stable the protein. In some embodiments, an inventive TIM-3 binding agent comprises a transition mid-point value ($T_m$) in vitro of about 60-100° C. For example, an anti-TIM-3 antibody agent can comprise a $T_m$ in vitro of about 65-80° C. (e.g., 66° C., 68° C., 70° C., 71° C., 75° C., or 79° C.), about 80-90° C. (e.g., about 81° C., 85° C., or 89° C.), or about 90-100° C. (e.g., about 91° C., about 95° C., or about 99° C.).

The biological activity of a particular TIM-3-binding antibody agent also can be assessed by determining its binding affinity to TIM-3 or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 picomolar (pM) to about 100 micromolar (μM) (e.g., from about 1 picomolar (pM) to about 1 nanomolar (nM), from about 1 nM to about 1 micromolar (μM), or from about 1 μM to about 100 μM). In some embodiments, an anti-TIM-3 antibody agent can bind to an TIM-3 protein with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In some embodiments, an anti-TIM-3 antibody agent can bind to TIM-3 with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values). Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, competitive binding assays, and/or ELISA (see, e.g., Janeway et al. (eds.), *Immunobiology*, 5th ed., Garland Publishing, New York, N.Y., 2001).

An anti-TIM-3 antibody agent may be administered alone or in combination with other drugs. For example, an anti-TIM-3 antibody agent can be administered in combination with other agents for the treatment or prevention of the diseases disclosed herein, such as agents that are cytotoxic to cancer cells, modulate the immunogenicity of cancer cells, or promote immune responses to cancer cells. In this respect, for example, an anti-TIM-3 antibody agent can be used in combination with at least one other anticancer agent including, for example, any chemotherapeutic agent known in the art, ionization radiation, small molecule anticancer agents, cancer vaccines, biological therapies (e.g., other monoclonal antibodies, cancer-killing viruses, gene therapy, and adoptive T-cell transfer), and/or surgery. In some embodiments, a subject (e.g., a mammal, e.g., a human) for treatment with an anti-TIM-3 antibody agent has been treated or will be treated with chemotherapy (e.g., platinum-based chemotherapy). In some embodiments, a chemotherapeutic agent is actinomycin, all-trans retinoic acid, azacitidine, azathioprine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, mechlorethamine, mercaptopurine, methotrexate, mitoxantrone, oxaliplatin, paclitaxel, pemetrexed, teniposide, tioguanine, topotecan, valrubicin, vemurafenib, vinblastine, vincristine, vindesine, or vinorelbine. In some such embodiments, a chemotherapeutic agent is a platinum-based chemotherapeutic agent, such as cisplatin, carboplatin, oxaliplatin, nedaplatin, triplatin tetranitrate, phenanthriplatin, picoplatin, or satraplatin. In some such embodiments, a chemotherapeutic agent is a folate antimetabolite such as pemetrexed. In some embodiments, a subject (e.g., a mammal, e.g. a human) for treatment with an anti-TIM-3 antibody agent has been treated or will be treated with an anti-angiogenic agent, for example, bevacizumab, itraconazole, carboxyamidotriazole, TNP-470, fumagillin, CM101, IL-12, platelet factor-4, suramin, SU5416, thrombospondin, angiostatic steroids, heparin, cartilage-derived angiogenesis inhibitory factor (e.g. peptide troponin I and chondromodulin I), matrix metalloproteinase inhibitor, angiostatin, endostatin, 2-methoxyestradiol, tecogalan, tetrathiomolybdate, thrombospondin, thalidomide, prolactin, αVβ3 inhibitor, lenalidomide, linomide, ramucirumab, tasquinimod, ranibizumab, sorafenib, sunitinib, pazopanib, everolimus, tissue inhibitors of metalloproteases (TIMP1 and TIMP2), bFGF soluble receptor, transforming growth factor beta, interferon alpha, interferon beta, soluble KDR and FLT-1 receptors, placental proliferin-related protein, pazopanib, sunitinib, sorafenib, axitinib, ponatinib, cabozantinib, regorafenib, vandetanib, lenvatinib, semaxanib, SU6668, vatalanib, tivozanib, cediranib, protamine, heparin, steroids, ascorbic acid ethers, sulfated polysaccharide DS 4152, fumagillin, AGM 12470, neovastat, RO4929097, MRK-003, MK-0752, PF03084014, MEDI0639, curcumin, 3,3'-diindolylmethane (DIM), resveratrol, 3,5-bis(2,4-difluorobenzylidene)-4-piperidone (DiFiD) and epigallocatechin-3-gallate (EGCG), honokiol, Flt2-11, CBO-P11, Je-11, V1, and any combination thereof. In some embodiments, an anti-TIM-3 antibody agent can be used in combination with an anti-inflammatory agent including, for example, corticosteroids (e.g., prednisone and fluticasone) and non-steroidal anti-inflammatory drugs (NSAIDs) (e.g., aspirin, ibuprofen, and naproxen).

In some embodiments, an anti-TIM-3 antibody agent is used to treat an infectious disease. When the inventive method treats an infectious disease, an anti-TIM-3 antibody agent can be administered in combination with at least one anti-bacterial agent or at least one anti-viral agent. In this respect, the anti-bacterial agent can be any suitable antibiotic known in the art. The anti-viral agent can be any vaccine of any suitable type that specifically targets a particular virus (e.g., live-attenuated vaccines, subunit vaccines, recombinant vector vaccines, and small molecule anti-viral therapies (e.g., viral replication inhibitors and nucleoside analogs).

In some embodiments, an anti-TIM-3 antibody agent is used to treat an autoimmune disease. When the inventive method treats an autoimmune disease, an anti-TIM-3 antibody agent can be used in combination with an anti-inflammatory agent including, for example, corticosteroids (e.g., prednisone and fluticasone) and non-steroidal anti-inflammatory drugs (NSAIDs) (e.g., aspirin, ibuprofen, and naproxen).

In some embodiments, when an anti-TIM-3 antibody agent is used to treat cancer or an infectious disease, the TIM-3 binding agent can be administered in combination with other agents that inhibit immune checkpoint pathways. For example, an anti-TIM-3 antibody agent can be administered in combination with agents that inhibit or antagonize the programmed death 1 protein (PD-1), lymphocyte activation gene-3 protein (LAG-3), and/or cytotoxic T-lymphocyte-associated protein 4 (CTLA-4) pathways. Combination treatments that simultaneously target two or more of these immune checkpoint pathways have demonstrated improved and potentially synergistic antitumor activity (see, e.g., Sakuishi et al., *J. Exp. Med.,* 207: 2187-2194 (2010); Ngiow et al., *Cancer Res.,* 71: 3540-3551 (2011); and Woo et al., *Cancer Res.,* 72: 917-927 (2012)). In some embodiments, an inventive TIM-3 binding agent is administered in combination with an agent that inhibits LAG-3 signaling and/or an agent that inhibits PD-1 signaling. In some embodiments, an inventive TIM-3 binding agent is administered to a subject that has been administered or will be administered an agent that inhibits LAG-3 signaling, such that the subject receives treatment with both. In some embodiments, an inventive TIM-3 binding agent is administered to a subject that has been administered or will be administered an agent that inhibits PD-1 signaling, such that the subject receives treatment with both. In some embodiments, a mammal that receives treatment an inventive TIM-3 agent has been or will receive treatment with an agent that inhibits PD-1 and an agent that inhibits LAG-3, such that the mammal receives all three.

In some embodiments, an inventive TIM-3 binding agent is administered in combination with an antibody that binds to LAG-3 and/or an antibody that binds to PD-1. In some embodiments, anti-PD-1 antibody is an antibody selected from the group consisting of: BGB-A317, BI 754091, IBI308, INCSHR-1210, JNJ-63723283, JS-001, MEDI-0680, MGA-012, nivolumab, PDR001, pembrolizumab, PF-06801591, REGN-2810, TSR-042, and derivatives thereof. In some embodiments, an agent that inhibits PD-1 is an anti-PD-L1/L2 agent. In some embodiments, an anti-PD-L1/L2 agent is an anti-PD-L1 antibody. In some embodiments, an anti-PD-L1 antibody agent is atezolizumab, avelumab, CX-072, durvalumab, FAZ053, LY3300054, PD-L1 millamolecule, or derivatives thereof.

In some embodiments, a subject is receiving or will receive one or more additional therapies in combination with a TIM-3-binding agent. In some embodiments, an additional therapy is a PARP inhibitor. In some embodiments, a PARP inhibitor is ABT-767, AZD 2461, BGB-290, BGP 15, CEP 8983, CEP 9722, DR 2313, E7016, E7449, fluzoparib (SHR 3162), IMP 4297, INO1001, JPI 289, JPI 547, monoclonal antibody B3-LysPE40 conjugate, MP 124, niraparib (ZEJULA) (MK-4827), NU 1025, NU 1064, NU 1076, NU1085, olaparib (AZD2281), ONO2231, PD 128763, R 503, R554, rucaparib (RUBRACA) (AG-014699, PF-01367338), SBP 101, SC 101914, Simmiparib, talazoparib (BMN-673), veliparib (ABT-888), WW 46, 2-(4-(Trifluoromethyl)phenyl)-7,8-dihydro-5H-thiopyrano[4,3-d]pyrimidin-4-ol, and salts or derivatives thereof. In some embodiments, a PARP inhibitor is niraparib, olaparib, rucaparib, talazoparib, and veliparib. In some embodiments, additional therapies include treatment with a composition that delivers an agent that inhibits PD-1 and treatment with a PARP inhibitor such that the subject receives treatment with all three. In some embodiments, additional therapies include treatment with a composition that delivers an agent that inhibits PD-1, treatment with a composition that delivers an agent that inhibits LAG-3, and treatment with a PARP inhibitor such that the subject receives treatment with all four.

In this respect, a method of treating a disorder that is responsive to TIM-3 inhibition (e.g., cancer or an infectious disease) in a mammal can further comprise administering to the mammal a composition comprising (i) an antibody that binds to a TIM-3 protein and (ii) a pharmaceutically acceptable carrier or a composition comprising (i) an antibody that binds to a PD-1 protein and (ii) a pharmaceutically acceptable carrier. Mammals include, e.g., mice, rats, rabbits, dogs, cats, cows, horses, non-human primates, and humans.

In addition to therapeutic uses, an anti-TIM-3 antibody agent described herein can be used in diagnostic or research applications. In this respect, an anti-TIM-3 antibody agent can be used in a method to diagnose a disorder or disease in which the improper expression (e.g., overexpression) or increased activity of TIM-3 causes or contributes to the pathological effects of the disease or disorder. In a similar manner, an anti-TIM-3 antibody agent can be used in an assay to monitor TIM-3 protein levels in a subject being tested for a disease or disorder that is responsive to TIM-3 inhibition. Research applications include, for example, methods that utilize an anti-TIM-3 antibody agent and a label to detect a TIM-3 protein in a sample, e.g., in a human body fluid or in a cell or tissue extract. An anti-TIM-3 antibody agent t can be used with or without modification, such as covalent or non-covalent labeling with a detectable moiety. For example, the detectable moiety can be a radioisotope (e.g., $^{3}H$, $^{14}C$, $^{32}P$, $^{35}S$, or $^{125}I$) a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antigen-binding agent (e.g., an antibody) to a detectable moiety may be employed in the context of the invention (see, e.g., Hunter et al., *Nature*, 194: 495-496 (1962); David et al., *Biochemistry*, 13: 1014-1021 (1974); Pain et al., *J. Immunol. Meth.*, 40: 219-230 (1981); and Nygren, *J. Histochem. and Cytochem.*, 30: 407-412 (1982)).

TIM-3 protein levels can be measured using an inventive TIM-3-binding agent by any suitable method known in the art. Such methods include, for example, radioimmunoassay (RIA), and FACS. Normal or standard expression values of TIM-3 can be established using any suitable technique, e.g., by combining a sample comprising, or suspected of comprising, TIM-3 with a TIM-3-specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, *Monoclonal Antibodies: A Manual of Techniques*, CRC Press, Inc. (1987)). The amount of TIM-3 polypeptide expressed in a sample is then compared with a standard value.

An anti-TIM-3 antibody agent can be provided in a kit, e.g., a packaged combination of reagents in predetermined amounts with instructions for performing a diagnostic assay. If an anti-TIM-3 antibody agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

Other features of the invention will become apparent in the course of the following descriptions of exemplary embodiments, which are given for illustration of the invention and are not intended to be limiting thereof.

EXEMPLIFICATION

Example 1—Description of Certain Exemplary Anti-TIM-3 Antibodies

This example describes particular anti-TIM-3 antibody heavy chain polypeptide and light chain polypeptide sequences and nucleic acids encoding the same.

```
An anti-TIM-3 antibody heavy chain polypeptide
                                       (SEQ ID NO: 1)
EVQLLESGGGLVQPGGSLRLSCAAASGFTFSSYDM

SWVRQAPGKGLDWVSTISGGGTYTYYQDSVKGRFT

ISRDNSKNTLYLQMNSLRAEDTAVYYCASMDYWGQ

GTTVTVSSASTKGPSVFPLAPCSRSTSESTAALGC

LVKDYFPEPVTVSWNSGALTSGVHTFPAVLQSSGL

YSLSSVVTVPSSSLGTKTYTCNVDHKPSNTKVDKR

VESKYGPPCPPCPAPEFLGGPSVFLFPPKPKDTLM

ISRTPEVTCVVVDVSQEDPEVQFNWYVDGVEVHNA

KTKPREEQFNSTYRVVSVLTVLHQDWLNGKEYKCK

VSNKGLPSSIEKTISKAKGQPREPQVYTLPPSQEE

MTKNQVSLTCLVKGFYPSDIAVEWESNGQPENNYK

TTPPVLDSDGSFFLYSRLTVDKSRWQEGNVFSCSV

MHEALHNHYTQKSLSLSLGK

An anti-TIM-3 antibody light chain polypeptide
                                       (SEQ ID NO: 2)
DIQMTQSPSSLSASVGDRVTITCRASQSIRRYLNW

YHQKPGKAPKLLIYGASTLQSGVPSRFSGSGSGTD

FTLTISSLQPEDFAVYYCQQSHSAPLTFGGGTKVE

IKRTVAAPSVFIFPPSDEQLKSGTASVVCLLNNFY

PREAKVQWKVDNALQSGNSQESVTEQDSKDSTYSL

SSTLTLSKADYEKHKVYACEVTHQGLSSPVTKSFN

RGEC

An anti-TIM-3 antibody heavy chain polypeptide
with a signal sequence
                                       (SEQ ID NO: 5)
MEFGLSWLFLVAILKGVQCEVQLLESGGGLVQPGG

SLRLSCAAASGFTFSSYDMSWVRQAPGKGLDWVST

ISGGGTYTYYQDSVKGRFTISRDNSKNTLYLQMNS

LRAEDTAVYYCASMDYWGQGTTVTVSSASTKGPSV

FPLAPCSRSTSESTAALGCLVKDYFPEPVTVSWNS

GALTSGVHTFPAVLQSSGLYSLSSVVTVPSSSLGT

KTYTCNVDHKPSNTKVDKRVESKYGPPCPPCPAPE

FLGGPSVFLFPPKPKDTLMISRTPEVTCVVVDVSQ

EDPEVQFNWYVDGVEVHNAKTKPREEQFNSTYRVV

SVLTVLHQDWLNGKEYKCKVSNKGLPSSIEKTISK

AKGQPREPQVYTLPPSQEEMTKNQVSLTCLVKGFY

PSDIAVEWESNGQPENNYKTTPPVLDSDGSFFLYS

RLTVDKSRWQEGNVFSCSVMHEALHNHYTQKSLSL

SLGK

An anti-TIM-3 antibody light chain
polypeptide with a signal sequence
                                       (SEQ ID NO: 6)
MDMRVPAQLLGLLLLWLRGARCDIQMTQSPSSLSA

SVGDRVTITCRASQSIRRYLNWYHQKPGKAPKLLI

YGASTLQSGVPSRFSGSGSGTDFTLTISSLQPEDF

AVYYCQQSHSAPLTFGGGTKVEIKRTVAAPSVFIF

PPSDEQLKSGTASVVCLLNNFYPREAKVQWKVDNA

LQSGNSQESVTEQDSKDSTYSLSSTLTLSKADYEK

HKVYACEVTHQGLSSPVTKSFNRGEC

Nucleotide sequence encoding anti-TIM-3
antibody heavy chain polypeptide
                                       (SEQ ID NO: 3)
GAG GTG CAG CTG TTG GAG TCT GGG GGA

GGC TTG GTA CAG CCT GGG GGG TCC CTG

AGA CTC TCC TGT GCA GCA GCC TCT GGA

TTC ACT TTC AGT AGC TAT GAC ATG TCT

TGG GTC CGC CAG GCT CCA GGG AAG GGG

CTG GAC TGG GTC TCA ACC ATT AGT GGT

GGT GGT ACT TAC ACC TAC TAT CAA GAC

AGT GTG AAG GGG CGG TTC ACC ATC TCC

AGA GAC AAT TCC AAG AAC ACG CTG TAT

CTG CAA ATG AAC AGC CTG AGA GCC GAG

GAC ACG GCC GTA TAT TAC TGT GCG TCC

ATG GAC TAC TGG GGG CAA GGG ACC ACG

GTC ACC GTC TCC TCA GCA TCC ACC AAG

GGC CCA TCG GTC TTC CCG CTA GCA CCC

TGC TCC AGG AGC ACC TCC GAG AGC ACA
```

```
GCC GCC CTG GGC TGC CTG GTC AAG GAC

TAC TTC CCC GAA CCA GTG ACG GTG TCG

TGG AAC TCA GGC GCC CTG ACC AGC GGC

GTG CAC ACC TTC CCG GCT GTC CTA CAG

TCC TCA GGA CTC TAC TCC CTC AGC AGC

GTG GTG ACC GTG CCC TCC AGC AGC TTG

GGC ACG AAG ACC TAC ACC TGC AAC GTA

GAT CAC AAG CCC AGC AAC ACC AAG GTG

GAC AAG AGA GTT GAG TCC AAA TAT GGT

CCC CCA TGC CCA CCA TGC CCA GCA CCT

GAG TTC CTG GGG GGA CCA TCA GTC TTC

CTG TTC CCC CCA AAA CCC AAG GAC ACT

CTC ATG ATC TCC CGG ACC CCT GAG GTC

ACG TGC GTG GTG GTG GAC GTG AGC CAG

GAA GAC CCC GAG GTC CAG TTC AAC TGG

TAC GTG GAT GGC GTG GAG GTG CAT AAT

GCC AAG ACA AAG CCG CGG GAG GAG CAG

TTC AAC AGC ACG TAC CGT GTG GTC AGC

GTC CTC ACC GTC CTG CAC CAG GAC TGG

CTG AAC GGC AAG GAG TAC AAG TGC AAG

GTC TCC AAC AAA GGC CTC CCG TCC TCC

ATC GAG AAA ACC ATC TCC AAA GCC AAA

GGG CAG CCC CGA GAG CCA CAG GTG TAC

ACC CTG CCC CCA TCC CAG GAG GAG ATG

ACC AAG AAC CAG GTC AGC CTG ACC TGC

CTG GTC AAA GGC TTC TAC CCC AGC GAC

ATC GCC GTG GAG TGG GAG AGC AAT GGG

CAG CCG GAG AAC AAC TAC AAG ACC ACG

CCT CCC GTG CTG GAC TCC GAC GGC TCC

TTC TTC CTC TAC AGC AGG CTA ACC GTG

GAC AAG AGC AGG TGG CAG GAG GGG AAT

GTC TTC TCA TGC TCC GTG ATG CAT GAG

GCT CTG CAC AAC CAC TAC ACA CAG AAG

AGC CTC TCC CTG TCT CTG GGT AAA

Nucleotide sequence encoding an anti-TIM-3
antibody light chain polypeptide
                                    (SEQ ID NO: 4)
GAC ATC CAG ATG ACC CAG TCT CCA TCC

TCC CTG TCT GCA TCT GTA GGA GAC AGA

GTC ACC ATC ACT TGC CGG GCA AGT CAG

AGC ATT AGG AGG TAT TTA AAT TGG TAT

CAC CAG AAA CCA GGG AAA GCC CCT AAG

CTC CTG ATC TAT GGT GCA TCC ACC TTG

CAA AGT GGG GTC CCA TCA AGG TTC AGT

GGT AGT GGA TCT GGG ACA GAT TTC ACT

CTC ACC ATC AGC AGT CTG CAA CCT GAA

GAT TTT GCA GTG TAT TAC TGT CAA CAG

AGT CAC AGT GCC CCC CTC ACT TTC GGC

GGA GGG ACC AAG GTG GAG ATC AAA CGA

ACT GTG GCT GCA CCA TCT GTC TTC ATC

TTC CCG CCA TCT GAT GAG CAA TTG AAA

TCT GGA ACT GCC TCT GTT GTG TGC CTG

CTG AAT AAC TTC TAT CCC AGA GAG GCC

AAA GTA CAG TGG AAG GTG GAT AAC GCC

CTC CAA TCG GGT AAC TCC CAG GAG AGT

GTC ACA GAG CAG GAC AGC AAG GAC AGC

ACC TAC AGC CTC AGC AGC ACC CTG ACG

CTG AGC AAA GCA GAC TAC GAG AAA CAC

AAA GTC TAC GCC TGC GAA GTC ACC CAT

CAG GGC CTC AGC TCG CCC GTC ACA AAG

AGC TTC AAC AGG GGA GAG TGT
```

The sequences above describe an exemplary humanized monoclonal anti-TIM-3 antibody utilizing a human IGHG4*01 heavy chain gene, and a human IGKC*01 kappa light chain gene, as scaffolds. There is a single Ser to Pro point mutation in the hinge region of the IgG4 heavy chain. This mutation is at the canonical S228 position, corresponding to residue 240 in SEQ ID NO: 5, which includes the signal sequence. Without wishing to be bound by theory, it is envisioned that this point mutation serves to stabilize the hinge of the antibody heavy chain.

The example further describes biophysical and biochemical characterization of this exemplary humanized monoclonal anti-TIM-3 antibody. Lys-C and trypsin digested peptides were well separated and detected by on-line LC-MS analysis. The disulfide bond linkages were confirmed by comparison of total ion chromatograms in the non-reduced (NR) condition with the reduced condition. Disulfide linkages are consistent with the expected disulfide linkage pattern for an IgG4 molecule. The residues involved in the expected inter- and intrachain disulfide linkages are tabulated below (Tables 1, 2 and 3).

TABLE 1

Expected residues involved in disulfide linkages of an exemplary anti-TIM-3 antibody agent heavy chain having an amino acid sequence as set forth in SEQ ID NO: 1.

| Cysteine residue ID | anti-TIM-3 mAb HC Residue (position in SEQ ID NO: 1) |
|---|---|
| I | 22 |
| II | 96 |
| III | 127 |
| IV | 140 |
| V | 196 |

TABLE 1-continued

Expected residues involved in disulfide linkages of an exemplary anti-TIM-3 antibody agent heavy chain having an amino acid sequence as set forth in SEQ ID NO: 1.

| Cysteine residue ID | anti-TIM-3 mAb HC Residue (position in SEQ ID NO: 1) |
|---|---|
| VI | 219 |
| VII | 222 |
| VIII | 254 |
| IX | 314 |
| X | 360 |
| XI | 418 |

TABLE 2

Expected residues involved in disulfide linkages of an exemplary anti-TIM-3 antibody agent light chain having an amino acid sequence as set forth in SEQ ID NO: 2.

| Cysteine residue ID | anti-TIM-3 mAb LC Residue (position in SEQ ID NO: 2) |
|---|---|
| I | 23 |
| II | 88 |
| III | 134 |
| IV | 194 |
| V | 214 |

TABLE 3

Exemplary disulfide bond assignments for an anti-TIM-3 antibody.

| Disulfide bond NO. | Disulfide-containing peptides | SEQ ID NO | Linkage site on HC (position in SEQ ID NO: 1) | Linkage site on LC (position in SEQ ID NO: 2) |
|---|---|---|---|---|
| DS1 | VTITCR=FSGSG SGTDFTLTISSL QPEDF AVYYCQQSHSAP LTFGGGTK | 7 8 | | 23 88 |
| DS2 | SGTASWCLLNNFYP R=VYACEVTHQG LSSPVTK | 9 | | 134 194 |
| DS3 | SFNRGEC=GPSV FPLAPCSR GEC=GPSVFPLA PCSR | 10 11 | 127 | 214 |
| DS4 | LSCAAASGFTFSS YDMSWVR=AEDTA VYYCASMDYWGQG TTVTVSSASTK | 12 13 | 22 97 | |
| DS5 | STSESTAALGCLV K=TYTCNVDHK STSESTAALGCLV K=TYTCNVDHK PSNTK | 14 15 | 140 196 | |
| DS6 | YGPPCPPCPAPE FLGGPSVFLFPP K=YGPPCPPCPA PEFLGGPSVFLF PPK YGPPCPPCPAPE FLGGPSVFLFPP K=YGPPCPPC PAPEFLGGPS VFLFPPKPK | 16 17 | 219 222 | |
| DS7 | TPEVTCVWDVSQE DPEVQFNWYVDGV EVHNAK=CK | 18 | 254 314 | |
| DS8 | NQVSLTCLV K=WQEGNVFS CSVMHEALHNH YTQK | 19 | 360 418 | |

LC: light chain; HC: heavy chain

This exemplary anti-TIM-3 antibody exhibits an occupied N-glycosylation site at asparagine residue 290 in the CH2 domain of each heavy chain in the mature protein sequence (SEQ ID NO:1). The expressed N-glycosylation at this site is a mixture of oligosaccharide species typically observed on IgGs expressed in mammalian cell culture, for example, shown below is the relative abundance of glycan species from a preparation of this exemplary anti-TIM-3 antibody cultured in Chinese Hamster Ovary (CHO) cells (Table 4).

TABLE 4

Glycan Analysis of an anti-TIM-3 antibody binding agent

| Species | Abundance (% of total oligosaccharide) | Description of Glycan |
|---|---|---|
| G0F | 20.1% | Core fucosylated agalactobiantennary complex-type oligosaccharide |
| G1F | 41.9% | Core fucosylated monogalactosylated biantennary complex type oligosaccharide |
| G2F | 29.0% | Core-fucosylated galactosylated biantennary complex type oligosaccharide |
| G2FS1 | 3.2% | Monosialylated core fucosylated galactosylated biantennary complex type oligosaccharide |
| G2FS2 | 1.2% | Disialylated core fucosylated galactosylated biantennary complex type oligosaccharide |
| M5 | 0.4% | Oligomannosidic N-linked oligosaccharide, $Man_5GlcNAc_2$ |

Example 2—Binding of an Exemplary Anti-TIM-3 Antibody to Recombinant TIM-3

This example describes binding of an exemplary anti-TIM-3 antibody (having heavy and light chains as set forth in SEQ ID NOs: 1 & 2, respectively) to recombinant TIM-3 polypeptides. Specifically, this example demonstrates high affinity binding of an exemplary antibody to soluble TIM-3 fusions and cell-expressed recombinant TIM-3 as determined using surface plasmon resonance (SPR) and flow cytometry, respectively.

SPR analyses were carried out using a Biacore T200, and kinetic constants were determined using Biacore T200 Evaluation software. Experimental parameters were chosen such that saturation was reached at the highest antigen concentrations and $R_{max}$ values were kept under 50 response units (RU). GE anti-mouse IgG (Fc-specific) was immobilized on a Biacore CM5 chip using EDC-activated amine coupling chemistry. Dimeric soluble human TIM-3 mIgG2a Fc was then captured onto this surface to a target capture level of ~70 RU or less. Next an exemplary anti-TIM-3 antibody (having heavy and light chains as set forth in SEQ ID NOs: 1 & 2, respectively) was flowed over the surface with captured antigen (TIM-3 fusion). Capture and analyte binding were performed in HBS-EP+ buffer. The captured antigen and antibodies were removed between each cycle to ensure a fresh binding surface for each concentration of antigen. The resulting sensorgrams were fitted globally using a 1:1 binding model to calculate on- and off-rates ($k_{assoc}$ and $k_{dissoc}$, respectively), and dissociation constants as a measure of overall affinity ($K_D$). SPR measurements demonstrated that an exemplary anti-TIM-3 antibody bound to both human and cynomolgus monkey TIM-3 with high affinity with $K_D$ estimates of 7 and 17 pM, respectively (Table 4). Further binding analyses determined that the exemplary anti-TIM-3 antibody did not substantially bind to human TIM-1 polypeptide or human PD-1 polypeptide (data not shown).

Flow cytometry studies were performed with CHO-K1 cell line clones in which native human or cynomolgus monkey TIM-3 was stably transfected. An exemplary anti-TIM-3 antibody (having heavy and light chains as set forth in SEQ ID NOs: 1 & 2, respectively) was diluted in 3-fold dilutions. Dilutions of exemplary antibody were added to human or cynomolgus monkey TIM-3 expressing CHO-K1 cells (1E5 cells) and incubated on ice. Cells were washed twice and incubated on ice with PE-conjugated goat anti-human IgG4 to detect antibody binding. Cells were washed and resuspended in the presence of propidium iodide to exclude dead cells and fixed before fluorescence was analyzed on a BD FACSArray (BD Biosciences). Data were analyzed for median fluorescence intensity, graphed, and curves fitted for $EC_{50}$ value calculation in GraphPad Prism (GraphPad Software, Inc.) using a non-linear (sigmoidal) regression analysis. This exemplary anti-TIM-3 antibody was found to bind to cell-surface human and cynomolgus monkey TIM-3 with an $EC_{50}$ of 0.17 and 0.27 nM, respectively (Table 5).

This example demonstrates that anti-TIM-3 antibodies within the scope of the present invention can specifically bind to TIM-3 polypeptides with high affinity.

Example 3—TIM-3 Blockade Enhances T Cell Activation in Exhausted Immune Cells

Figure 2A:
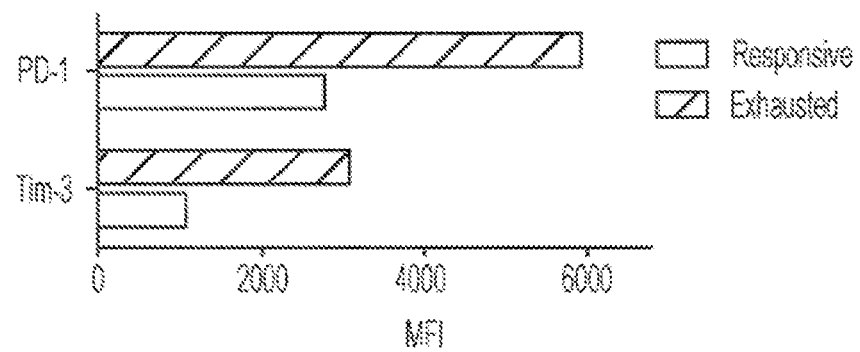
FIGS. 2A and 2B depict results from an exemplary in vitro T cell exhaustion model.

This example describes characterization of an exemplary anti-TIM-3 antibody agent in an in vitro T-cell exhaustion model characterized by increased expression of PD-1 and TIM-3 (FIG. 2A). Specifically, spleen was removed from MBP-Tracker mice and processed to generate single cell suspension of splenocytes. Cells were resuspended at $3\times10^6$/mL and stimulated with WT-MBP or APL-MBP for 72 hours. Following stimulation, T cells were purified by ficoll density gradient and subsequently re-plated at $2\times10^6$/mL in 20 U/mL IL-2 for four days. After 4 days, cells were collected, resuspended ($4\times10^5$/mL, final $2\times10^4$ per well) and restimulated using irradiated APC (from B10PLxC57BL/6 mice, $4\times10^6$/mL, final $2\times10^5$ per well) a single dose of APL-MBP peptide, together with test or reference substance or appropriate controls for 72 hours. Culture supernatants were collected and stored frozen for subsequent assessments.

Figure 2B:
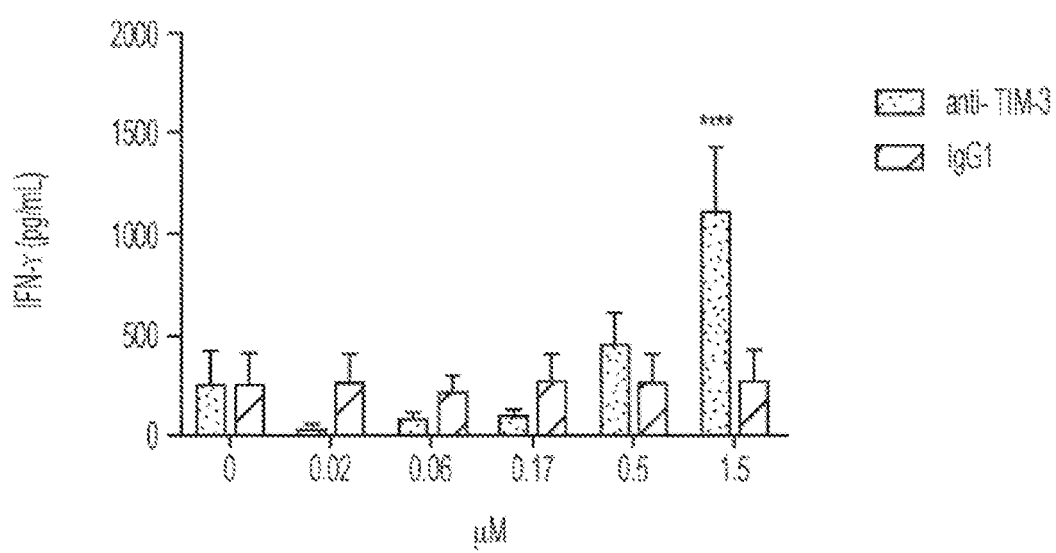

Assessment of cytokine production by ELISA indicated that TIM-3 blockade significantly enhanced IFN-γ production in this system (FIG. 2B). Accordingly, this example demonstrates that anti-TIM-3 antibodies can activate exhausted immune cells.

Having thus described at least several aspects and embodiments of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description are by way of example only and the invention is described in detail by the claims that follow.

All references, including publications, patent applications, and patents, cited herein are hereby incorporated by reference to the same extent as if each reference were individually and specifically indicated to be incorporated by reference and were set forth in its entirety herein. The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the

TABLE 5

Binding of exemplary anti-TIM-3 antibody to TIM-3 by Surface Plasma Resonance (SPR) and TIM-3 Expressing CHO-K1 cells

| Species | Kinetic Parameters (SPR) | | | TIM-3 expressing CHO-K1 cells |
|---|---|---|---|---|
| | $K_{assoc}$ (Ms)$^{-1}$ | $K_{dissoc}$ (s$^{-1}$) | $K_D$ (pM) | $EC_{50}$ (nM) |
| Human | $1.5 \times 10^7$ | $1.1 \times 10^{-4}$ | 7 | 0.17 |
| Cynomolgus monkey | $1.1 \times 10^7$ | $1.9 \times 10^{-4}$ | 17 | 0.27 |

$K_{assoc}$ = association rate constant;
$K_{dissoc}$ = dissociation rate constant;
$K_D$ = dissociation constant.

listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. An antibody that binds T Cell Immunoglobulin and Mucin Protein 3 (TIM-3), said antibody comprising: a heavy chain polypeptide comprising the amino acid sequence of SEQ ID NO: 1; and a light chain polypeptide comprising the amino acid sequence of SEQ ID NO: 2.

2. A composition comprising the antibody of claim 1 and a pharmaceutically acceptable carrier.

3. A method of treating a cancer or infection in a human that is responsive to TIM-3 binding agents, which method comprises administering to the human an effective amount of the antibody of claim 1, whereupon the cancer or infection is treated in the human.

4. The method of claim 3, wherein the method comprises treating the cancer.

5. The method of claim 4, wherein the cancer is selected from the group consisting of: endometrial cancer, breast cancer, ovarian cancer, cervical cancer, colorectal cancer, and lung cancer.

6. The method of claim 4, wherein the cancer is non-small cell lung cancer.

7. The method of claim 3, wherein the method further comprises administering to the human an agent that inhibits Programmed Cell Death 1 (PD-1).

8. The method of claim 7, wherein the agent that inhibits PD-1 is nivolumab.

9. The method of claim 7, wherein the agent that inhibits PD-1 is pembrolizumab.

10. The method of claim 7, wherein the agent that inhibits PD-1 is TSR-042.

11. The method of claim 3, wherein the method further comprises administering to the human an agent that inhibits lymphocyte-activation gene 3 (LAG-3).

12. The method of claim 3, wherein the method further comprises administering to the human an agent that inhibits poly (ADP-ribose) polymerase (PARP).

13. A method of manufacturing the antibody of claim 1, said method comprising expressing a nucleic acid encoding the antibody in a host cell culture.

14. A nucleic acid encoding a polypeptide comprising the amino acid sequence of SEQ ID NO: 1 or SEQ ID NO: 2.

15. A vector comprising the nucleic acid of claim 14.

16. An isolated cell comprising the vector of claim 15.

17. The nucleic acid of claim 14, wherein the nucleic acid encodes a polypeptide comprising the amino acid sequence of SEQ ID NO: 1 and the amino acid sequence of SEQ ID NO: 2.

18. The nucleic acid of claim 14, wherein the nucleic acid encodes a polypeptide comprising the amino acid sequence of SEQ ID NO: 5 and the amino acid sequence of SEQ ID NO: 6.

19. A nucleic acid comprising the nucleic acid sequence of SEQ ID NO:3 or SEQ ID NO:4.

* * * * *